United States Patent [19]

Ito et al.

[11] Patent Number: 4,987,147

[45] Date of Patent: Jan. 22, 1991

[54] 6-[P-[5-(1-IMIDAZOLYL)PENTYLOXY]-PHENOXY]-2,2-DIMETHYL-HEXANOIC ACID COMPOUNDS WHICH ARE USEFUL IN TREATING TUMORS

[75] Inventors: Noriki Ito, Saitama; Yoshinobu Nagano; Akihiro Tanaka, both of Tokyo; Yoso Numasaki, Saitama; Koichiro Takahashi, Tokyo, all of Japan

[73] Assignee: Yamanouchi Pharmaceutical Co., Ltd., Tokyo, Japan

[21] Appl. No.: 349,226

[22] Filed: May 9, 1989

Related U.S. Application Data

[62] Division of Ser. No. 74,290, Jul. 16, 1987, Pat. No. 4,891,432.

[30] Foreign Application Priority Data

Jul. 24, 1986 [JP] Japan .................................. 61-174774

[51] Int. Cl.⁵ .................. C07D 233/60; A61K 31/415
[52] U.S. Cl. ..................................... 514/399; 548/341
[58] Field of Search ......................... 548/341; 514/399

[56] References Cited

FOREIGN PATENT DOCUMENTS 0130077  1/1985  European Pat. Off. ............ 548/341

OTHER PUBLICATIONS

Chemical Abstracts, vol. 100, No. 23, Abstract 185,312c, Jun. 4, 1984, p. 16.
Chemical Abstracts, vol. 103, No. 19, Abstract 160,441t, Nov. 11, 1985, 706.

*Primary Examiner*—Frederick E. Waddell
*Assistant Examiner*—Zinna Northington-Davis
*Attorney, Agent, or Firm*—Burgess, Ryan & Wayne

[57] ABSTRACT

Novel phenoxy derivatives are provided such as 6-[p-5-(1-imidazolyl)pentyloxy]phenoxy]-2,2-dimethyl-hexanoic acid, pharmaceutical compositions containing the derivative and their use in treating tumors.

1 Claim, No Drawings

6-[P-[5-(1-IMIDAZOLYL)PENTYLOXY]PHENOXY]-2,2-DIMETHYL-HEXANOIC ACID COMPOUNDS WHICH ARE USEFUL IN TREATING TUMORS

This is a division of application Ser. No. 074,290, filed July 16, 1987 now U.S. Pat. No. 4,891,432.

The present invention relates to novel phenoxy derivatives represented by general formula (I):

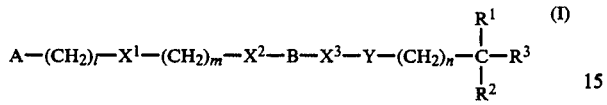

wherein:

A is a biphenyl group, an unsubstituted or substituted monocyclic 5- or 6-membered heterocyclic ring which contains 1 to 4 nitrogen atom(s) and may additionally contain an oxygen atom or a sulfur atom, or an unsubstituted or substituted bicyclic 9- or 10-membered heterocyclic ring which contains 1 to 4 nitrogen atom(s) and may additionally contain an oxygen atom or a sulfur atom;

l represents 0 or an integer of 1 to 3;
m represents an integer of 1 to 10;
n represents 0 or an integer of 1 to 9;
$X^1$ represents a single bond, an oxygen atom, a sulfur atom, or a sulfinyl group;
$X^2$ represents an oxygen atom, a sulfur atom, or a sulfinyl group;
$X^3$ represents an oxygen atom, a sulfur atom, or a sulfinyl group;
B represents a phenylene group

a 1,3,4-thiadiazo2,5-diyl group

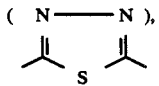

a pyrimididene group

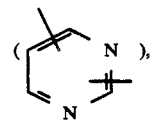

or a pyridazinidene group

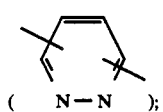

Y represents a single bond, or a carbonyl group;
$R^1$ represents a hydrogen atom, or a lower alkyl group;
$R^2$ represents a hydrogen atom, or a lower alkyl group;
$R^3$ represents a carboxyl group, a lower alkoxycarbonyl group which maybe substituted with a phenyl group(s), an unsubstituted or substituted aminocarbonyl group, a cyano group, a hydroxyl group, or a hydrogen atom; with the proviso that the following case-(1l, and case-(2) compounds are excluded:

(1) a formula I compound wherein, when A—(CH$_2$)$_l$—X$^1$ is a 1-imidazolyl group, m is 3 or 5, —X$^2$—B—X$^3$— is a

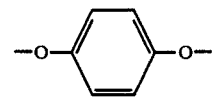

group, (a) Y is a single bond, n is 3, 4 or 5, $R^1$ is a methyl group, $R^2$ is a methyl group, and $R^3$ is a methoxycarbonyl group or an ethoxycarbonyl group; or
(b) Y is a single bond, n is 0, one of $R^1$ and $R^2$ is a hydrogen atom and the other of $R^1$ and $R^2$ is an ethyl group, and $R^3$ is an ethoxycarbonyl group; or
(c) Y is a carbonyl group, n is 0, $R^1$ is a methyl group, $R^2$ is a methyl group, and $R^3$ is a hydrogen (2) a formula 1 compound wherein A is a 3-pyridyloxy group, m is 3, —X$^2$—B—X$^3$— is a

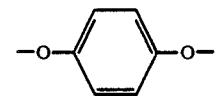

group, Y is a single bond, n is 3 or 5, $R^1$ is a methyl group, $R^2$ is a methyl group and $R^3$ is a methoxycarbonyl group.

This invention further relates to a medicament particular a medicament for preventing or treating tumors, said medicament comprising an effective amount of compound formula I.

Among the compounds which fall under the above formula (I), some compounds are described in Published (unexamined) Japanese Applications 136563-85 and 113178-83. However, in these Published Applications, same of the formula (I) compounds are shown only generically (that is, neither working examples nor physical data for the compounds are disclosed); and, as to the utility, there is only mention of the utility of the compounds for inhibiting platelet aggregation.

"An unsubstituted or substituted monocyclic 5- or 6-membered heterocylic ring which contains 1 to 4 nitrogen atom(s) and may additionally contain an oxygen atom or a sulfur atom" in the definition of A in the formula (I) means a nitrogen-atom-containing monocyclic 5- or 6-membered heterocyclic ring group which ring contains 1, 2, 3 or 4 nitrogen atom(s), and may additionally contain one atom selected from an oxygen atom or a sulfur atom, and which ring may contain one substituent. These heterocyclic ring may be saturated or may have unsaturated bond or bonds. Specific examples of monocyclic 5- or 6-membered heterocyclic ring include a 1-imidazolyl group, a 1-pyrrolyl group, a 1-pyrazolyl group, a 5-tetrazolyl group, a 1-triazolyl group, a 2-imidazolin-4-yl group

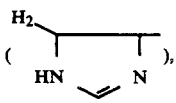

a 2H-pyrrolyl group

a 2H-pyrrolidinyl group

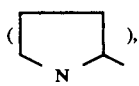

a 3-pyridyl group, a 2-pyrimidyl group, a 2-piperidyl group, a 2-pyridinyl group, a 2-thiazolyl group, a dihydrothiazolyl group

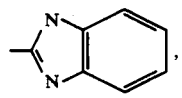

a 3-isothiazolyl group, a 2-oxazolyl group, a 2-thiadiazolyl group, a 3-morpholinyl group.

"An unsubstituted or substituted dicyclic 9- or 10-membered heterocylic ring which contains 1 to 4 nitrogen atom(s) and may additionally contain an oxygen atom or a sulfur atom in the definition of A is, for example, 2-benzimidazolyl

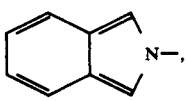

2-isoindolyl

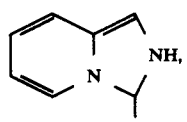

2,3-dihydroimidazo[1,5-a]-pyrrdin-3-yl

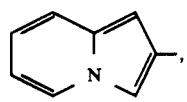

2-indolydinyl

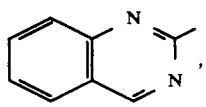

6-purinyl, 9-purinyl

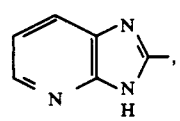

1-benzoimidazolyl, 1H-imidazo[4,5-b]pyridin-2-yl

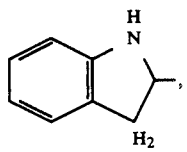

2-indolynyl

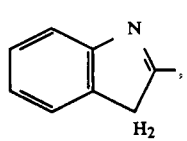

3H-indolyl

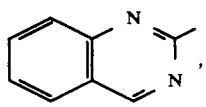

2-isoquinolyl, 2-quinazolynyl 2-benzothiazolyl; or 2-benzooxazolyl.

The above monocyclic ordicyclic heterocyclic ring may have a substituent, and examples of the substituent are hydroxy, mercapto, lower alkyl, lower alkylthio, carboxy lower alkylthio, lower alkoxycarbonyl lower alkylthio, nitro, etc. Further, N-oxide compounds are also listed as such substituted heterocyclic ring compounds of this invention.

The compounds represented by general formula (I) described above form salts with acids or bases, which salts the present invention encompasses. Examples of the salts with acids include salts with inorganic acids such as hydrochloric acid, hydrobromic acid, hydroiodic acid, sulfuric acid, etc., salts, with organic acid such as formic acid, acetic acid, lactic acid, oxalic acid, succinic acid, fumaric acid, maleic acid, citric acid, benzoic acid, methanesulfonic acid, p-toluene-sulfonic acid, benzenesulfonic acid, etc., and quaternary ammonium salts with alkyl halides such as methyl iodide, etc. Examples of the salts with bases include salts with inorganic bases such as sodium salt, potassium salt, calcium salt, etc., and salts with organic bases such as triethyl amine salt, etc.

The formula (I) compounds and their salts of this invention possess excellent anti-tumor activity but have low toxicity and are therefore effective for use as anti-tumor agents or medicaments for preventing or treating tumors and for reducing or preventing metastasis of tumors.

The pharmacological activity, toxicity, etc. of formula (I) compounds are shown below, together with test methods used.

Test 1

Effectiveness against mouse leukemia L1210 cells (in vitro test).

A suspension of cells in culuture medium was transferred into wells in a microplate in an amount of $1 \times 10^5$ L1210-cells/well. Test sample diluted with a culture medium was added to the suspension in each well, and the mixture was incubated on the medium at 37° C. for 3 days in an atmosphere of air containing 5% carbon dioxide.

Thereafter, the incubated cells were recovered from the microplate and the number of live cells was counted by the dye exclusion test using a 0.5% solution of trypan blue and by using a hemocytometer. The cytotoxicity effects against L1210 cells were evaluated by the mean dose producing 50%-killing of tumor cells ($IC_{50}$) ($\mu M$). The cytotoxicity data for the test compounds are given in Table 1.

Test 2

Anti-tumor test against Ehrlich solid tumor Ehrlich tumor cells, $2 \times 10^6$, on Day 7 After intraperitoneal transplantation to ddY/SLC mice, were subcutaneously transplanted in the left abdomen of ddY/SLC mice (5 week age, male) - 10 to a group. The active component was intraperitoneally administered in a definite dose 24 hours after the transplantation. (administration: once per one day; 1 through 9 days)

The tumor growth inhibition was assessed by measuring the weight of each tumor on day 21 after the transplantation, and determing a tumor growth inhibition rate of the group administered with the active component to the control group according to the following equation:

growth inhibition rate (%)=(C−T)/C×100

T: mean tumor weight in the active
component-administered group
C: mean tumor weight in the control group The results data are shown in Table 1.

TABLE 1

| Test Compound | Test 1 $IC_{50}$ ($\mu M$) | Test 2 Growth Inhibition Rate (%) | |
|---|---|---|---|
| Example 1 | 7.2 | 68.5* | (100 mg/kg) |
| 2 | 7.5 | 52.9* | ( 50 mg/kg) |
| 3 | 4.0 | 58.5* | ( 50 mg/kg) |
| 4 | 4.9 | 50.1* | (100 mg/kg) |
| 5 | 6.3 | 39.3 | (100 mg/kg) |
| 6 | 6.8 | 43.8 | (100 mg/kg) |
| 7 | 11.0 | 45.0 | (100 mg/kg) |
| 9 | 12.0 | 30.7 | (100 mg/kg) |
| 10 | — | 23.7 | (100 mg/kg) |
| 11 | 40.0 | 33.4 | (100 mg/kg) |
| 12 | 8.5 | | |
| 13 | 7.6 | | |
| 14 | 4.2 | | |
| 15 | 28.9 | 38.8 | (100 mg/kg) |
| 16 | 8.2 | 42.2* | (100 mg/kg) |
| 17 | 13.7 | 36.6* | ( 50 mg/kg) |
| 18 | 9.5 | 34.9* | (100 mg/kg) |
| 19 | 5.7 | 47.6* | (100 mg/kg) |
| 20 | 8.2 | 52.8* | (100 mg/kg) |
| 22 | 6.7 | 40.2* | (100 mg/kg) |
| 23 | 6.1 | | |
| 24 | 20.6 | 31.7* | (100 mg/kg) |
| 25 | 23.5 | | |
| 26 | 42.7 | 30.0* | (100 mg/kg) |
| 27 | 4.2 | | |
| 28 | 18.9 | | |
| 29 | 9.0 | | |
| 30 | 2.3 | 60.9* | (100 mg/kg) |
| 31 | 2.6 | 48.9* | (100 mg/kg) |
| 32 | 2.2 | 57.5* | (100 mg/kg) |
| 33 | 7.7 | 59.5* | (100 mg/kg) |
| 34 | 4.0 | | |
| 35 | 8.6 | 35.9* | (100 mg/kg) |
| 36 | 3.8 | | |
| 37 | 4.6 | | |
| 38 | 10.0 | 39.3* | (100 mg/kg) |
| 39 | 4.1 | | |
| 40 | | 46.9* | (100 mg/kg) |
| 41 | 7.4 | 38.7* | (100 mg/kg) |
| 42 | 4.4 | 53.1* | ( 50 mg/kg) |
| 43 | 8.0 | 55.5* | (100 mg/kg) |
| 44 | 3.7 | 46.1* | (100 mg/kg) |
| 45 | 42.5 | | |
| 48 | 5.5 | 46.3 | (100 mg/kg) |
| 49 | 5.5 | | |
| 50 | 1.8 | | |
| 51 | 0.6 | 42.5* | ( 50 mg/kg) |
| 52 | 3.6 | 55.7* | (100 mg/kg) |
| 53 | 4.3 | 49.3* | (100 mg/kg) |
| 55 | 3.8 | 63.1* | ( 50 mg/kg) |
| 56 | 13.8 | 30.2 | (100 mg/kg) |
| Ex. 57 | 9.2 | 23.1 | (100 mg/kg) |
| 58 | — | 27.7 | (100 mg/kg) |
| 59 | 5.3 | 38.9 | (100 mg/kg) |
| 60 | 3.7 | 40.5 | ( 50 mg/kg) |
| 61 | 5.9 | 38.9 | (100 mg/kg) |
| 62 | 10.9 | 9.0 | (12.5 mg/kg) |
| 63 | 3.5 | | |
| 64 | 2.6 | | |
| Control (5-Fluorouracil) | 0.41 | 61.0 | ( 25 mg/kg) |

*$P < 0.05$

Test 3

Test against mouse mammalian MM-46 tumor MM-46 tumor cells, $1 \times 10^6$, on day 6 after intraperitonal transplantation to $C^3H$/He/SLC mice, were intraperitoneally transplanted to $C_3H$/He/SLC mice (6 week age, male) - 10 mice to a group. The active component was orally administered in a definite dose 24 hours after the transplantation according to the schedule shown in Table 2. The tumor growth inhibition was evaluated as the percentage of the median survival day of the administered group versus that of the control group, according to the following equation.

T/C %=T/C×100

T: median survival day of the administered group
C: median survival day of the control group

Test 4

Anti-tumor test against mouse M15076 solid tumor. M5076 Tumor cells, $1 \times 10^6$, on day 14 after intraperitoneal transplantation to C57BL16/cRJ mice, were subcutaneously transplanted to the left abdomen of BDF1/SLC mice (8 week age, male) -10 mice to a group (20 mice for the control group). The active component was orally administered in a definite dose 24 hours after the transplantation according to the schedule shown in Table 3. The tumor growth inhibition was assessed by measuring the weight of each tumor on days 14 after the transplantation, and determining the tumor growth inhibition rate of the active component-administered group to the control group, according to the following equation Similarly to the above, the same active component was intraperitoneally administered, and no example of death was noted up to a dose of 800 mg/kg. Accordingly, the acute toxicity of the Compound in the case of intraperitoneal administration is greater than 800 mg/kg.

TABLE 2

| Test Compound | Dose (mg · kg) | Route for Administration and Days Given | Median Survival Day | T/C (%) | No. of 20-day Survivors |
| --- | --- | --- | --- | --- | --- |
| Ex. 45 | 100 | p.o. (1–6 days) | 8.0 | 114.3 | 0/10 |
|  | 200 | as above | 8.0 | 114.3 | 0/10 |
|  | 400 | as above | 8.0 | 114.3 | 0/10 |
|  | 800 | p.o. (1–8 days) | 10.0 | 142.9 | 0/10 |
| Tetrahydro-furyl-5-fluoro-uracil | 100 | p.o. (1–6 days) | 6.0 | 85.7 | 0/10 |
|  | 200 | as above | 7.0 | 100 | 0/10 |
| Control |  |  | 7.0 | 100 | 0/10 |

TABLE 3

| | | | Day 14 | |
| --- | --- | --- | --- | --- |
| Test Compound | Dose (mg/kg) | Route for Administration and Days Given | Weight of Tumor (g) | Growth Inhibition Rate (%) |
| Ex. 45 | 100 | p.o. (1–9 days) | 0.53 ± 0.09 | 13.1 |
|  | 200 | as above | 0.49 ± 0.14 | 19.7* |
|  | 400 | as above | 0.54 ± 0.12 | 11.5 |
|  | 800 | as above | 0.47 ± 0.09 | 23.0** |
| Tetrahydro-furyl-5-fluorouracil | 100 | as above | 0.52 ± 0.19 | 14.8 |
|  | 200 | as above | 0.37 ± 0.08 | 39.3*** |
| Control |  |  | 0.61 ± 0.13 |  |

*P < 0.05, P < 0.01, *P < 0.00.

Growth inhibition rate (%) = (C−T)/C × 100

T: mean tumor weight in the active-component-administered group
C: mean tumor weight on the control group

Test 5

Antitumor test against Ehrlich solid tumor Ehrlich tumor cells, 3×10$^6$, on Day 6 after intraperitoneal transplantation to ddY/SLC mice, were subcutaneously transplanted in the left abdomen of ddY/SLC mice (5 week age, male) - 10 mice to a group (37 mice for the control group). The active component was intraperitoneally administered in a definite dose 24 hours after the transplantation, according to the scheduled shown in Table 4. The tumor growth inhibition was assessed by measuring the weight of each tumor on the 21th day after transplantation, and determing the tumor growth inhibition rate of the active component-administered group to the control group, according to the following equation.

Growth inhibition rate (%) = (C−T)/C × 100

T: mean tumor weight in the active-component-administered group
C: mean tumor weight on the control group

Toxicity Test

The active component (the Compound of Example 45) as orally administered to ddY mice (mean body weight of 30 g, male). No example of death was noted up to a dose of 1,600 mg/kg. Accordingly, the acute toxicity of the Compound is greater than 1,600 mg/kg (oral administration).

TABLE 4

| | | | Day 21 | |
| --- | --- | --- | --- | --- |
| Test Compound | Dose (mg/kg) | Route for Administration and Days Given | Weight of Tumor (g) | Growth Inhibition Rate (%) |
| Ex. 45 | 50 | Intraperitoneal adminstration (1 to 9 days) | 2.81 ± 1.55 | 29.9 |
|  | 100 | as above | 2.04 ± 1.26 | 49.1* |
|  | 200 | as above | 1.46 ± 0.50 | 63.6** |
|  | 400 | as above | 1.70 ± 0.60 | 57.6** |
| 5-Fluoro-uracil | 12.5 | as above | 2.55 ± 1.21 | 36.4 |
|  | 25 | as above | 2.18 ± 0.96 | 45.6* |
| Control |  |  | 4.01 ± 2.22 |  |

*P < 0.05, **P < 0.01

The suitable daily dose of the antitumor agents of this invention for adults is 500 to 2,000 mg (as active ingredient), preferably 800 to 1,200 mg, when administered orally or as suppository, which is subdivided into 1 to 4 doses. The optimum dose should be determined case by case within the range mentioned above depending on the age and conditions of the patient, other drugs to be used in combination, and other factors.

The agents may be administered orally in the form of tablets, capsules, granules or syrup, while suppositories and injections may be used for parenteral administration. As examples of excipients to be used in oral preparations, there may be mentioned lactose, starch, talc, magnesium stearate, microcrystalline cellulose, carboxymethylcellulose and hydroxypropylcellulose. Bases used for preparing suppositories include polyethylene glycol, lanolin, cacao butter and Witeb Sol ® (Dinamit Nobel).

An example of capsule preparation is shown below

| (Formulation) | |
|---|---|
| Compound of Example 51 | 200 mg |
| Lactose | 205 mg |
| Crystalline cellulose | 50 mg |
| Hydroxypropylcellulose | 15 mg |
| Starch | 25 mg |
| Magnesium stearate | 5 mg |
| | 500 mg |

The active ingredient, lactose and crystalline cellulose were mixed, am aqueous solution of hydroxycellulose was added, and the mixture was kneaded and subjected to granulation process. The granules thus prepared were dried, h and magnesium stearate were admixed, and the resulting granules were filled in No. 1 gelatin capsules.

Synthetic Methods

The compounds of this invention can be synthesized according to the methods shown below.

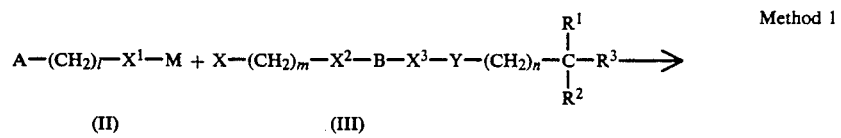

Method 1

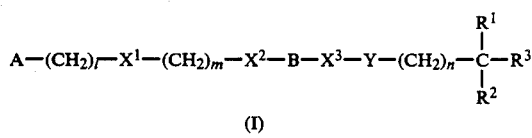

(I)

(wherein A, $X^1$, $X^2$, $X^3$, B, Y, l, m, n, $R^1$, $R^2$ and $R^3$ are as defined above; M denotes hydrogen atom or an alkali metal; and X stands for a halogen atom.)

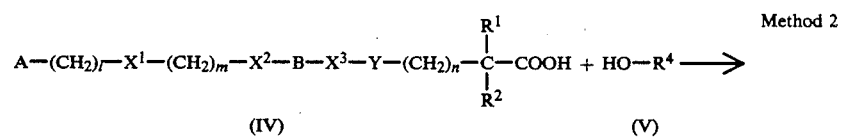

Method 2

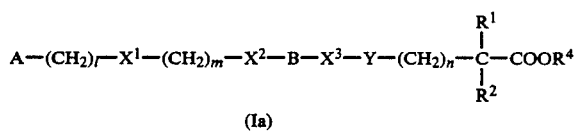

(Ia)

(wherein $R^4$ is a lower alkyl which may optionally be substituted by an aryl group.)

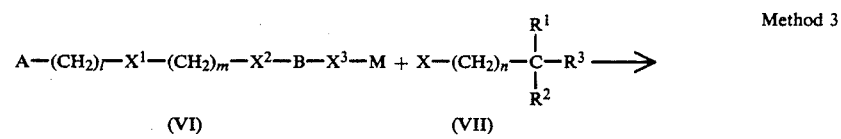

Method 3

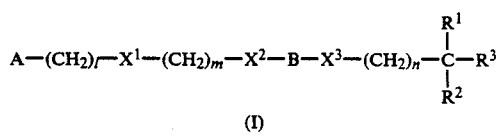

(I)

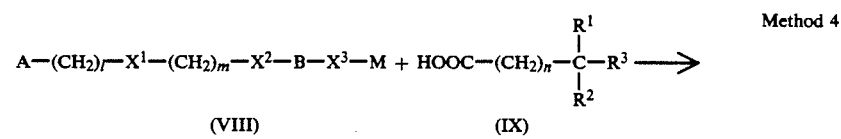

Method 4

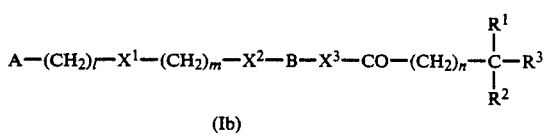

(Ib)

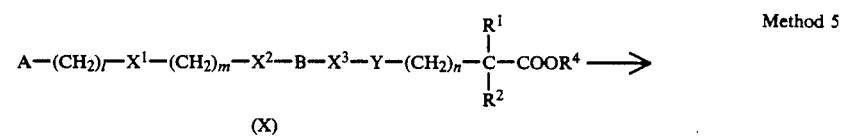

Method 5

-continued $$A-(CH_2)_l-X^1-(CH_2)_m-X^2-B-X^3-Y-(CH_2)_n-\underset{R^2}{\overset{R^1}{\underset{|}{\overset{|}{C}}}}-COOH$$

(Ic)

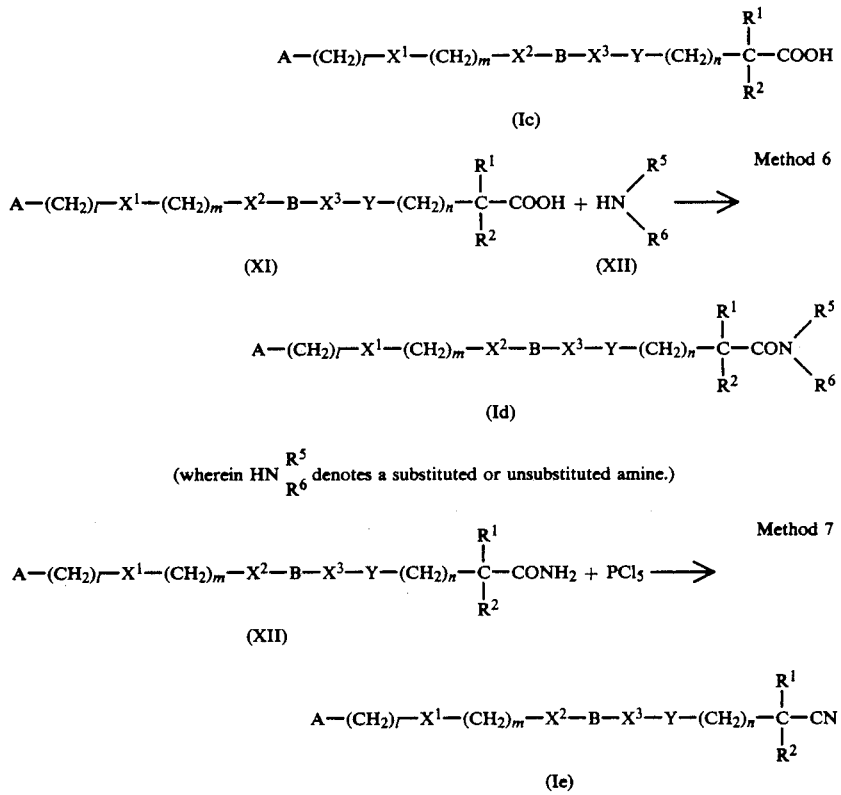

$$A-(CH_2)_l-X^1-(CH_2)_m-X^2-B-X^3-Y-(CH_2)_n-\underset{R^2}{\overset{R^1}{\underset{|}{\overset{|}{C}}}}-CN$$

(Ie)

Each of the above synthetic methods will be detailed below.

Method 1

Compounds of this invention represented by formula (I) can be prepared by reaction of a compound (II) with a compound (III). The reaction is preferably carried out in an inert organic solvent (e.g., alcohols such as methanol and ethanol, dimethyl sulfoxide, dimethylformamide, benzene, toluene, xylene, diethyl ether and tetrahydrofuran) at room temperature or at an elevated temperature.

When a compound (II) in which M is hydrogen atom is used, the reaction is preferably conducted in the presence of a base. Preferred examples of the base include alkali metal hydrides such as sodium hydride, alkali metal alcoholates such as sodium ethoxide, and organic lithium compounds such as n-butyl lithium.

Method 2

The compounds of this invention represented by formula (Ia) can be prepared by esterification between a carboxylic acid of formula (IV), or a reactive derivative thereof, and an alcohol of formula (V), or a reactive derivative thereof. Preferable reactive derivatives of carboxylic acid (IV) are the corresponding acid halides and acid anhydrides, while preferred reactive derivatives of alcohol (V) are esters thereof with toluenesulfonic and methanesulfonic acids. Generally, it is better to use an alcohol itself (V) (not a reactive derivative thereof) for the esterification reaction. In this case, a carboxylic acid (IV) is allowed to react with an equimolar or slight excess amount of the alcohol (V) in an inert organic solvent (e.g., benzene, toluene, xylene, diethyl ether, tetrahydrofuran, chloroform, dichloromethane and dichloroethane) in the presence of a Lewis acid catalyst (e.g., hydrochloric acid, sulfuric acid, trifluoroacetic acid, boron trifluoride etherate and p-toluenesulfonic acid), or in the presence of a condensation agent (e.g., N,N'-dicyclohexylcarbodiimide and 1-carbonylimidazole). Alternatively, an acid halide or acid anhydride of carboxylic acid (IV) is allowed to react with an equimolar or slight excess amount of the alcohol (V) in an inert organic solvent (e.g., diethyl ether, tetrahydrofuran and acetonitrile) in the presence of a base (e.g., N,N-diemthylaniline, pyridine, triethylamine, sodium carbonate and potassium carbonate).

Method 3

Compounds of this invention (I) can also be prepared by reaction of an alkyl halide of formula (VII) with a phenol (or thiophenol) of formula (VI) in the presence of a base, or with that phenol (or thiophenol) in the form of an alkali metal phenolate (or thiophenolate).

Iodine, bromine and chlorine may be mentioned as the halogen atom in the alkyl halides (VII), and sodium and potassium are preferred examples of the alkali metal. The reaction is preferably carried out in an inert organic solvent (e.g., alcohols such as methanol and ethanol, dimethyl sulfoxide, dimethylformamide benzene, xylene, tetrahydrofuran, acetone and methyl ethyl ketone) at room temperature or at an elevated temperature.

When a phenol or thiophenol of formula (VI) is allowed to react with an alkyl halide (VII), potassium carbonate, sodium amide, caustic soda or sodium hydride is preferably used as the base.

Method 4

This is a method for preparing the compounds represented by formula (Ib) compounds (I) of this invention in which Y is carbonyl group. The reaction involved is esterification between a phenol (or thiophenol) of formula (VIII) and a substituted-alkylcarboxylic acid of formula (IX), which can be effected in the same manner as Method 2.

Method 5

This is a method for preparing compounds of formula (Ic) by hydrolysis of an ester of formula (X). The hydrolysis can be easily effected by treating a solution of compound (X) in an organic solvent (e.g., methanol and ethanol) with an aqueous alkaline solution (e.g., an aqueous solution of caustic soda) at an elevated temperature.

Method 6

The compounds represented by formula (Id) compound (I) of this invention in which $R^3$ is aminocarbonyl radical can be prepared by reaction of a carboxylic acid of formula (XI), or a reactive derivative thereof, with an amine of formula (XII).

The reactive derivatives of compounds (XI) include acid halides such as acid chlorides and acid bromides; acid azides; active esters, such as esters with N-hydroxybenzotriazole, p-nitrophenol and p-chlorophenol; symmetric acid anhydrides; mixed acid anhydrides, such as those obtained by reaction of a carboxylic acid (XI) with an alkyl halogenocarbonate (e.g., isobutyl chlorocarbonate, methyl chlorocarbonate and ethyl bromocarbonate).

When a compound (XI) is used as starting material in the form of free acid, the reaction is preferably carried out in the presence of a condensation agent, such as N,N'-dicyclohexylcarbodiimide and 1,1-carbonyldiimidazole. When a reactive derivative of compound (XI) is used, addition of a base, such as tertiary amines (e.g., triethylamine, pyridine, picoline, lutidine and N,N-dimethylaniline) and inorganic bases (e.g., potassium carbonate, sodium carbonate, caustic soda and caustic potash), is effective in accelerating the reaction in some instances.

The type of solvent used and temperature conditions should be properly selected case by case depending on the type of reactive derivative and other factors.

Method 7

The compounds represented by formula (Ie) compounds (I) of this invention in which $R^3$ is cyano radical can be prepared by treating an acid amide of formula (XII) with a dehydrating agent, such as phosphorus pentachloride, phosphorus pentoxide and thionyl chloride.

The compounds of this invention thus formed are isolated and purified as such or in the form of a salt by commonly used techniques, such as crystallization, distillation, extraction, various types of chromatography and recrystallization.

EXAMPLES OF THE INVENTION

The following Examples will further illustrate the invention. Some of the starting materials used in these Examples are novel compounds, and their synthetic methods are also described in Reference Examples.

Reference Example 1

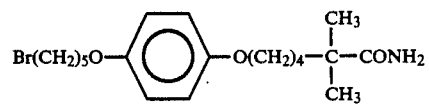

A mixture of 3.0 g 6-(4-hydroxyphenoxy)-2,2-dimethylhexanamide, 50 ml ethanol, 2.5 g potassium carbonate and 3.6 g 1,5-dibromopentane was heated under reflux overnight with stirring. The solvent was distilled off under reduced pressure, the residue was extracted with chloroform, the extract was washed with water and worked up as usual. The crude product thus obtained was purified by silica gel column chromatography, affording 2.90 g of 6-[p-(5-bromopentyloxy)-phenoxy]-2,2-dimethylhexanamide.

Physicochemical Properties (1) Melting point 113°–115° C.
(2) NMR spectrum (CDCl$_3$)
  δ: 1.20 (6H, s), 3.44 (2H, t), 3.90 (2H, t), 3.92 (2H, t), 6.84 (4H, s), 1.32–2.12 (12H, m)
(3) IR spectrum (cm$^{-1}$)
  1640, 1610, 1220

Compounds of Reference Example 2 through 4 given below were prepared in the same manner as above.

Reference Example 2

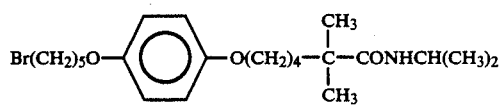

6[p-(5-Bromopenyloxy)phenoxy]-2,2-dimethylhexanoic acid isopropylamide

Physicochemical Properties (1) Oil
(2) NMR spectrum (CDCl$_3$)
  δ: 1.10 (6H, d), 1.14 (6H, s), 1.32–2.12 (12H, m), 3.44 (2H, t), 3.76–4.04 (5H, m) 6.80 (4H, s)
(3) IR spectrum (cm$^{-1}$)
  1620, 1220

Reference Example 3

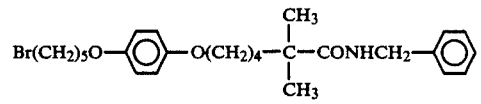

6-[p-(5-Bromopentyloxy)phenoxy]-2,2-dimethylhexanoic acid benzylamide

Physicochemical Properties (1) Oil
(2) NMR spectrum (CDCl$_3$)
  δ: 1.20 (6H, s), 1.32–2.12 12H, m , 3.44 (2H, t), 3.72–4.04 (4H, m), 4.44 (2H, d), 6.80 (4H, s), 7.28 (5H, s)
(3) IR spectrum (cm$^{-1}$) 1625, 1215

Reference Example 4

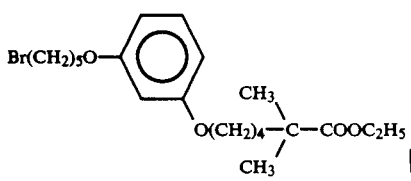

Ethyl 6-[m-(5-bromopentyloxy)phenoxy]-2,2-dimethylhexanoate

Physicochemical Properties
(1) Oil
(2) NMR spectrum (CDCl$_3$)
  δ: 1.18 (6H, s), 4.10 (2H, q), 1.24 (3H, t), 3.44 2H, t)

(3) IR spectrum (cm$^{-1}$)
  1720, 1590, 1280, 1260, 1140

Example 1

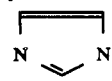 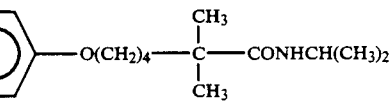

Imidazole (0.34 g), DMF (5 ml) and 60% sodium hydride in oil (0.25 g) were mixed with stirring under ice cooling, stirring was continued at room temperature for 30 minutes, and the mixture was cooled in ice once again. To this ice-cooled mixture was added with stirring a solution of 2.0 g 6-[p-(5-bromopentyloxy)phenoxy]-2,2-dimethylhexanamide in 5 ml DMF, and the resulting mixture was stirred at room temperature for three hours.

The solvent DMF was distilled off under reduced pressure, the residue was extracted with chloroform, the extract was washed with water and worked up as usual. The crude product thus obtained was purified by silica gel column chromatography, affording 1.45 g of 6-[p-[5-(1-imidazolyl) pentyloxy]phenoxy]-2,2-dimethylhexanamide.

Physicochemical Properties
(1) Melting point 118°–120° C.
(2) NMR spectrum (CDCl$_3$)
  δ: 1.20 (6H, s), 1.32–2.04 (12H, m), 3.76–4.08 (6H, m), 6.80 (4H, m), 6.90 (1H, m), 7.04 (1H, m), 7.46 (1H, s)

(3) IR spectrum (cm$^{-1}$)
  1640, 1610, 1215

Compounds of Examples 2 through 4 shown below were prepared in the same manner as above.

EXAMPLE 2

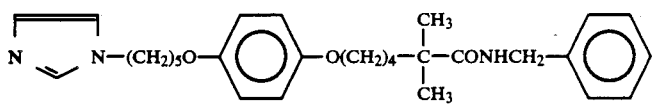

6-[p-[5-(1-Imidazolyl)pentyloxy]phenoxy]-2,2-dimethylhexanoic acid isopropylamide Physicochemical Properties
(1) Melting point 76°–78° C.
(2) NMR spectrum (CDCl$_3$)
  δ: 1.94 (6H, d), 1.20 (6H, s), 1.28–2.08 (12H, m), 3.72–4.12 (7H, m), 6.82 (4H, s), 6.92 (1H, m), 7.06 (1H, m), 7.46 (1H, s)
(3) IR spectrum (cm$^{-1}$)
  1620, 1210

EXAMPLE 3

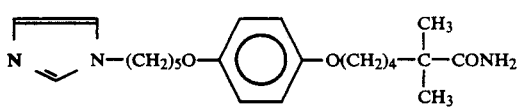

6-[p-[5-(1-Imidazolyl)pentyloxy]phenoxy]-2,2-dimethylhexanoic acid benzylamide

Physicochemical Properties
(1) Oil
NMR spectrum (CDCl$_3$)
  δ: 1.20 (6H, s), 1.28–2.08 (12H, m), 3.72–4.08 (6H, m), 4.42 (2H, d), 6.78 (4H, s), 6.90 (1H, m), 7.04 (1H, m), 7.26 (5H, s), 7.44 (1H, s)
(3) IR spectrum (cm$^{-1}$)
  1630, 1210

EXAMPLE 4

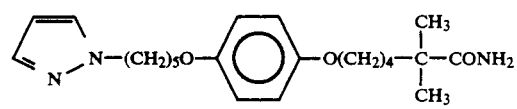

6-[p-[5-(1-Pyrazolyl)pentyloxy]phenoxy]-2,2-dimethylmide

Physicochemical Properties
(1) Melting point 90°–93° C.
(2) NMR spectrum (CDCl$_3$)
  δ: 1.20 (6H, s), 1.28–2.16 (12H, m), 3.88 (2H, t), 3.90 (2H, t), 4.16 (2H, t), 6.24 (1H, t), 6.76 (4H, s), 7.36 (1H, d), 7.50 (1H, d)
(3) IR spectrum (cm$^{-1}$)
  1635, 1610, 1215

EXAMPLE 5

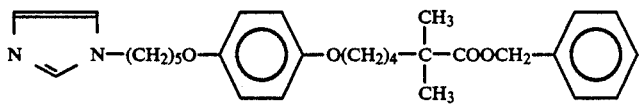

To a mixture of 0.90 g 6-[p-[5-(1-imidazolyl)pentyloxy]phenoxy]-2,2-dimethylhexanoic acid, 10 ml dichloromethane, 0.24 ml benzyl alcohol and 30 mg dimethylaminopyridine, was added with stirring 0.46 g dicyclohexylcarbodiimide at room temperature, and stirring was continued for five days. The urea which separated out was filtered off, and the filtrate was washed with 0.1N caustic soda solution and then with water. After dehydration, the solvents were distilled off, and the residue was purified by silical gel column chromatography, affording 1.05 g of benzyl 6-[p-[5-(1-imidazolyl)pentyloxy]phenoxy]-2,2-dimethylhexanoate.

Physicochemical Properties (1) NMR spectrum (CDCl$_3$)
  δ: 1.20 (6H, s), 1.30–2.10 (12H, m), 3.70–4.10 (6H, m), 5.10 (2H, s), 6.78 (4H, s), 6.90 (1H, s), 7.04 (1H, s), 7.32 (5H, s), 7.44 (1H, s)
(2) IR spectrum (cm$^{-1}$)
  1720, 1680, 1620, 1225

The compound of Example 6 shown below was prepared in the same manner as in Example 5.

EXAMPLE 6

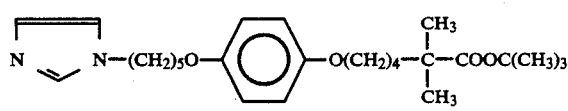

t-Butyl 6-[p-[5-(1-imidazolyl)pentyloxy]phenoxy]-2,2-dimethylhexanoate.

Physicochemical Properties (1) NMR spectrum (CDCl$_3$)
  δ: 1.20 (6H, s), 1.24 (9H, s), 1.32–2.12 (12H, m), 3.66–4.14 (6H, m), 6.76 (4H, s), 6.88 (1H, m), 7.02 (1H, m), 7.44 (1H, s)
(3) IR spectrum (cm$^{-1}$)
  1720, 1680, 1620 1225

EXAMPLE 7

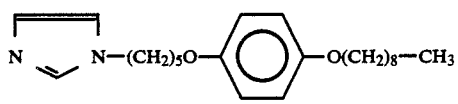

To a mixture of 2.46 g p-[5-(1-imidazolyl)pentyloxy]phenol, 24 ml ethanol and 1.75 g potassium carbonate, was added 2.1 g 1-bromonoane, and the resulting mixture was heated under reflux with stirring for two days. The solvent was distilled off under reduced pressure, the residue was extracted with chloroform, and the extract was washed with water, dehydrated and concentrated. The crude product thus obtained was purified by silica gel column chromatography, affording 0.88 g of [p-[5-(1-imidazolyl)pentyloxy]phenoxy]nonane.

Physicochemical Properties (1) Melting point 45°–47° C.
(2) NMR spectrum (CDCl$_3$)
  δ: 0.90 (3H, t), 1.10–2.10 (20H, m), 3.90–4.10 (6H, m), 6.80 (4H, s), 6.90 (1H, m), 7.06 (1H, m), 7.48 (1H, s)
(3) IR spectrum (cm$^{-1}$)
  1230

Compounds of Examples 8 and 9 given below were prepared in the same manner as above.

EXAMPLE 8

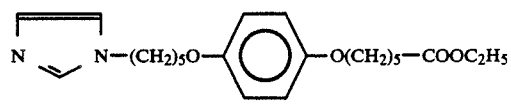

Ethyl 6-[p-[5-(1-imidazolyl)pentyloxy]phenoxy]hexanoate

Physicochemical Properties (1) NMR spectrum (CDCl$_3$)
  δ: 1.24 (3H, t), 1.36–2.04 (12H, m), 2.34 (2H, t), 3.76–4.08 (6H, m), 4.14 (2H, q), 680 (4H, s), 6.90 (1H, m), 7.06 (1H, m), 7.46 (1H, s)
IR spectrum (cm$^{-1}$)
  1720, 1230

EXAMPLE 9

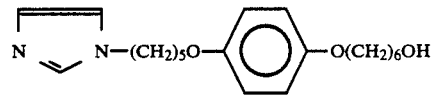

6-[p-[5-(1-Imidazolyl)pentyloxy]phenoxy]hexanol

Physicochemical Properties (1) Melting point 98°–101° C.
(2) NMR spectrum (CDCl$_3$)
  δ: 1.20–2.04 (14H, m), 3.56–3.76 (2H, m), 3.76–4.10 (6H, m), 6.80 (4H, s), 6.90 (1H, m), 7.06 (1H, m), 7.46 (1H, s)
(3) IR spectrum (cm$^{-1}$)
  1220

EXAMPLE 10

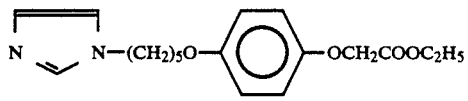

To a solution of 2.46 g p-[5-(1-imidazolyl)pentyloxy]phenol and 1.2 ml ethyl bromoacetate in 25 ml anhydrous N,N-dimethylformamide, was added under ice cooling and with stirring 440 mg of 60% sodium hydride in oil, and stirring was continued at room temperature for ten minutes. The solvent was distilled off, the residue was dissolved in chloroform, and the solution was washed with water and dried over anhydrous sodium sulfate. After distilling off, the chloroform, the residue was purified by silical gel column chromatography, affording 2.7 g of ethyl p-[5-(1-imidazolyl)pentyloxy]phenoxyacetate as oil.

Physicochemical Properties (1) NMR spectrum (CDCl$_3$)
  δ: 1.30 (3H, t), 3.92 (4H, q), 4.26 (H, q), 4.26 (2H, q), 4.55 (2H, s), 6.80 (4H, s), 6.90 (1H, m), 7.05 (1H, m), 7.46 (1H, s)

(2) Mass spectrum (EI)
  m/z: 332(M+), 259, 196, 137, 109

(3) IR spectrum (cm$^{-1}$); KBr
  1750, 1665, 1500, 1380, 1190, 1070, 830, 750

EXAMPLE 11

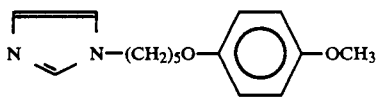

To a solution of 1.87 g p-[5-(1-imidazolyl)pentyloxy]phenol and 0.46 ml methyl iodide in 18 ml anhydrous N,N-dimethylformamide, was added under ice cooling and with stirring 290 mg of 60% sodium hydride in oil, and stirring was continued at room temperature for five minutes. Ethyl acetate was added to the reaction mixture, the precipitate which separated out was filtered off, and the filtrate was washed with water and dried over anhydrous sodium sulfate. The solvent was distilled off, and the residue was purified by silica gel column chromatography [chloroform/methanol/methanol/28% ammonia water (50:1:0.1)], affording 2.0 g of 1-[5-(1-imidazolyl)pentyloxy]-4-methoxybenzene as oil.

Physicochemical Properties (1) NMR spectrum (CDCl$_3$)
  δ: 3.76 (3H, s), 6.80 (4H, s), 6.90 (1H, m), 7.05 (1H, m), 7.45 (1H, s)

(2) Mass spectrum (EI)
  m/z: 261 (M+30 1), 137, 95, 81

EXAMPLE 12

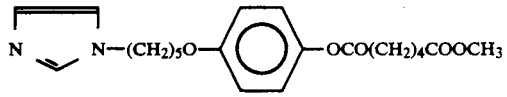

To a mixture of 0.74 g p-[5-(1-imidazolyl)pentyloxy]phenol, 0.53 g monomethyl adipate, 40 mg dimethylaminopyridine and 15 ml dichloromethane, was added with stirring 0.68 g dicyclohexyl carbodiimide at room temperature, and stirring was continued for two days. The urea which separated out was filtered off, and the filtrate was washed with water and dried. The solvent was distilled off, and the residue was purified by silica gel column chromatography, affording 0.99 g of 6-[p-[5-(1-imidazolyl)pentyloxyoxy]phenoxy]-6-oxohexanoate.

Physicochemical Properties

NMR spectrum (CDCl$_3$)
  δ: 1.10–2.10 (14H, m), 2.10–2.70 (4H, m), 3.68 (3H, s), 3.80–4.10 (4H, m), 6.76–7.04 (5H, m), 7.06 (1H, m), 7.50 (1H, s)

(2) IR spectrum (cm$^{-1}$)
  1730, 1690, 1610, 1240

EXAMPLE 13

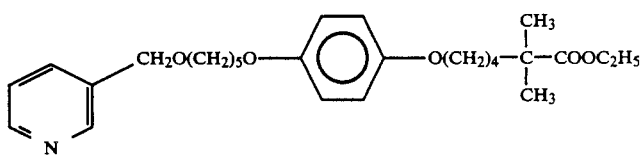

To a mixture of 0.71 g 4'-(5-(3-pyridylmethyloxy)-pentyloxy]phenol, 14 ml ethanol and 0.43 g potassium carbonate, was added with stirring 0.62 g ethyl 6-bromo-2,2-dimethylhexanoate, and the resulting mixture was heated under reflux for two days. The solvent was distilled off under reduced pressure, the residue was extracted with chloroform, and the extract was washed with water and dried. The chloroform was distilled off, and the residue was purified by silica gel column chromatography, affording 0.49 g of ethyl 6-[p-[5-(3-pyridylmethyloxy)pentyloxy]phenoxy]-2,2-dimethylhexanoate.

Physicochemical Properties (1) NMR spectrum (CDCl$_3$)
  δ: 1.16 (64H, s), 1.24 (3H,t), 1.34–2.00 (12H, m), 3.52 (2H, t), 3.90 (2H, t), 3.92 (2H, t), 4.12 (2H, q), 4.52 (2H, s), 6.80 (4H, s), 7.16–7.26 (1H, m), 7.56–7.80 (1H, m), 8 44–8.64 (2H, m)

(2) IR spectrum (cm$^{-1}$)
  1720, 1225

Compounds of Examples 14 through 18 shown below were prepared in the same manner as above

EXAMPLE 14

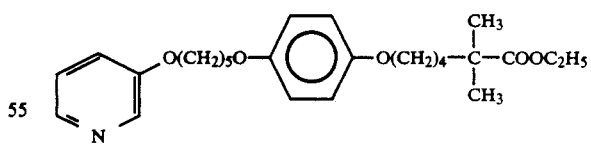

Ethyl 6-[p-[5-(3-pyridyloxy)pentyloxy]phenoxy]-2,2-dimethylhexanoate.

Physicochemical Properties (1) Melting point 46°–48° C.
(2) NMR spectrum (CDCl$_3$)
  δ: 1.16 (6H, s), 1.22 (3H, t), 1.32–2.08 (12H, m), 3.76–4.18 (8H, m), 6.80 (4H, s), 7.16–7.30 (2H, m), 8.16–8.36 (2H, m)
(3) IR spectrum (cm$^{-1}$)
  1710, 1290, 1230

EXAMPLE 15

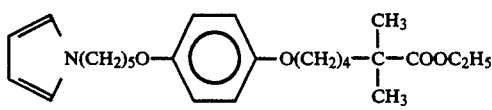

Ethyl 6-[p-[5-(1-pyrrolyl)pentyloxy]phenoxy]-2,2-dimethylhexanoate.

Physicochemical Properties (1) NMR spectrum (CDCl$_3$)
   δ: 1.16 (6H, s), 1.22 (3H, t), 1.36–2.04 (12H, m), 3.76–4.04 (6H, m), 4.12 (2H, q), 6.12 (2H, t), 6.64 (2H, t), 6.78 (4H, s)
(2) IR spectrum (cm$^{-1}$)
   1720, 1225

EXAMPLE 16

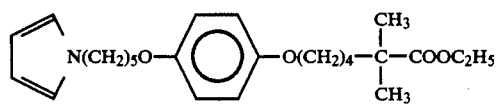

Ethyl 6-[p-[5-(1-pyrazolyl)pentyloxy]phenoxy]-2,2-dimethylhexanoate.

Physicochemical Properties (1) NMR spectrum (CDCl$_3$)
   δ: 1.16 (6H, s), 1.24 (3H, t), 1.36–2.12 (12H, m), 3.72–4.28 (8H, m), 6.24 (1H, t), 6.80 (4H, s), 7.38 (1H, m), 7.50 (1H, m)
(2) IR spectrum (cm$^{-1}$)
   1715, 1225

EXAMPLE 17

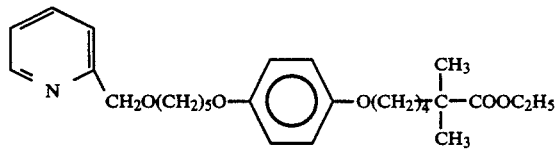

Ethyl 6-[p-[5-(2-pyridylmethyloxy)pentyloxy]-phenoxy]2,2-dimethylhexanoate.

Physicochemical Properties (1) NMR spectrum (CDCl$_3$)
   δ: 1.16 (6H, s), 1.20 (3H, s), 1.32–1.92 (12H, m), 3.56 (2H, t), 3.86 (2H, t), 3.88 (2H, t), 4.08 (2H, q), 4.40 (2H, s), 6.78 (4H, s), 7.04–7.76 (3H, m), 8.52 (1H, m)
(2) IR spectrum (cm$^{-1}$)
   1720, 1230

EXAMPLE 18

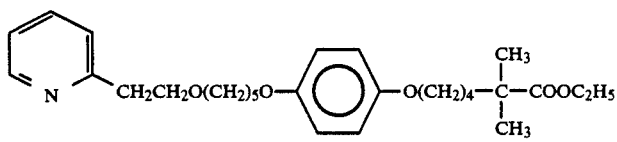

Ethyl 6-[p-[5-(2-pyridylethyloxy)pentyloxy]-phenoxy]-2,2-dimethylhexanoate.

Physicochemical Properties (1) NMR spectrum (CDCl$_3$)
   δ: 1.16 (6H, s), 1.20 (3H, s), 1.32–1.88 (12H, m), 3.02 (2H, t), 3.42 (2H, t), 3.68–3.96 (6H, m), 4.08 (2H, q), 6.68 (4H, s), 6.96–7.26 (2H, m), 7.44–7.64 (1H, m), 8.40–8.56 (1H, m)
(2) IR spectrum (cm$^{-1}$)
   1715, 1220

EXAMPLE 19

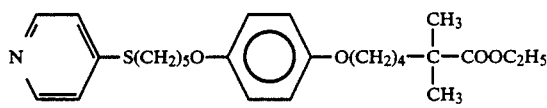

To a mixture of 1.08 g 6-[p-5-bromopentyloxy)-phenoxy]-2,2-dimethylhexanoate and 10 ml methanol, was added dropwise with stirring a solution of 0.34 g 4-mercaptopyridine and 0.26 g sodium bicarbonate in 5 ml water at room temperature, and the resulting mixture was gently heated under reflux for two hours. The methanol was distilled off under reduced pressure, the residue was extracted with chloroform, and the extract was washed with water and worked up as usual. The organic layer was dehydrated, the chloroform was distilled off, and the residue was purified by silica gel column chromatography, affording 0.68g of ethyl 6-[p-[5-(4-pyridylmercapto)pentyloxy]phenoxy]-2,2-dimethylhexanoate.

Physicochemical Properties (1) NMR spectrum (CDCl$_3$)
   δ: 1.20 (6H, s), 1.24 (3H, t), 1.32–2.04 (12H, m), 3.00 (2H, t), 3.76–4.00 (4H, m), 4.12 (2H, q), 6.82 (4H, s), 7.10 (2H, dd), 8.38 (2H, dd)
IR spectrum (cm$^{-1}$)
   1720, 1230

Compounds of Examples 20 and 21 shown below were prepared in the same manner as above.

EXAMPLE 20

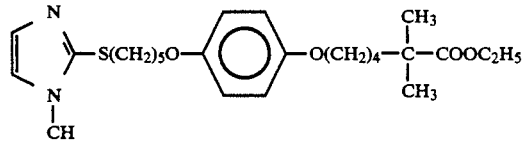

Ethyl 6-[p-[5-[2-(1-methyl)imidazolylthio]pentyloxy]-phenoxy]-2,2-dimethylhexanoate.

Physicochemical Properties

NMR spectrum (CDCl$_3$)
   δ: 1.18 (6H, s), 1.22 (3H, t), 1.36–2.00 (12H, m), 3.06 (2H, t), 3.58 (3H, s), 3.88 (4H, t), 4.10 (2H, q), 6.76 (4H, s), 6.94 (1H, d), 7.10 (1H, d)
(2) IR spectrum (cm$^{-1}$)

EXAMPLE 21

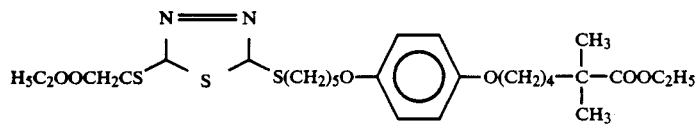

Ethyl 6-[p-[5-[2-(5-ethoxycarbonylmethylthio)-1,3,4-thiadiazolylthio]pentyloxy]phenyl]-2,2-dimethylhexanoate

Physicochemical Properties (1) NMR spectrum (CDCl$_3$)
δ: 1.16 (6H, s), 1.22 (3H, t), 1.24 (3H, t), 1.36–2.08 (12H, m), 3.30 (2H, t), 3.72–4.00 (4H, m), 4.06 (2H, s), 4.00–4.40 (4H, m), 6.78 (4H, s)

(2) IR spectrum (cm$^{-1}$)
1715, 1220

EXAMPLE 22

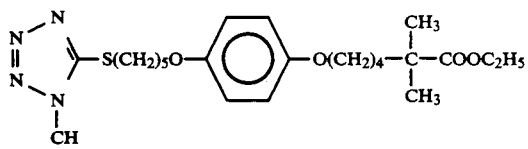

To a mixture of 1.08 g 6-[p-(5-bromopentyloxy)-phenoxy]-2,2-dimethylhexanoate and 10 ml methanol, was added with stirring sodium salt of 1-methyl-5-mercaptotetrazole (0.42 g), and the resulting mixture was heated under reflux for two hours. The methanol was distilled off under reduced pressure, the residue was extracted with chloroform, and the extract was washed with water and dried. The chloroform was distilled off, and the residue was purified by silica gel column chromatography, affording 0.54 g of ethyl 6-[p-[5-(1-methyl-5-tetrazolylmercapto)pentyloxy]phenoxy]-2,2-dimethylhexanoate.

Physicochemical Properties (1) NMR spectrum (CDCl$_3$)
δ: 1.16 (6H, s), 1.22 (3H, t), 1.36–2.08 (12H, m), 3.20–3.52 (2H, m), 3.76–4.00 (7H, m), 4.12 (2H, q), 6.78 (4H, s)

(2) IR spectrum (cm$^{-1}$)
1720, 1230

Compound of Example 23 shown below was prepared in the same manner as above.

EXAMPLE 23

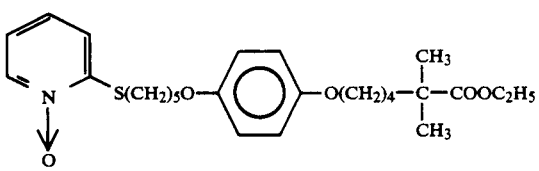

Ethyl 6-[p-[5-(N-oxo-2-pyridylthio)pentyloxy]phenoxy]-2,2-dimethylhexanoate

Physicochemical Properties (1) Melting point 55°–57° C.

(2) Elemental analysis (C$_{26}$H$_{37}$NO$_5$S)

|       | C (%) | H (%) | N (%) |
|-------|-------|-------|-------|
| Calcd.| 65.65 | 7.84  | 2.94  |
| Found | 65.48 | 7.99  | 2.73  |

(3) NMR spectrum (CDCl$_3$)
δ: 1.16 (6H, s), 1.20 (3H, t), 4.10 (2H, q), 6.78 (4H, s)

EXAMPLE 24

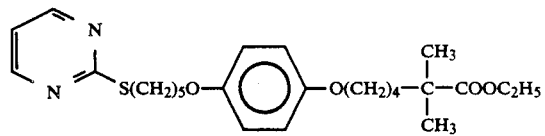

To a mixture of 523 mg 2-mercaptopyrimidine and 25 ml anhydrous N,N-diemthylformamide, were added 640 mg anhydrous potassium carbonate and 2 g ethyl 6-[p-(5-bromopentyloxy)phenoxy]-2,2-dimethylhexanoate, and the resulting mixture was stirred at room temperature for 12 hours. The solvent was distilled off under reduced pressure, the residue was extracted with chloroform, and the extract was washed with water and dried. The chloroform was distilled off, and the residue was purified by silica gel column chromatography (chloroform), affording 740 mg ethyl 6-[p-[5-(2-pyrimidylthio)pentyloxy]phenoxy]-2,2-dimethylhexanoate as oil.

Physicochemical Properties (1) NMR spectrum (CDCl$_3$)
δ: 1.14 (6H, s), 1.22 (3H, t), 3.16 (2H, t), 4.10 (2H, q), 6.76 (4H, s), 6.90 (1H, dd)

(2) IR spectrum (cm$^{-1}$)
1720, 1560, 1545, 1380

Compounds of Examples 25 through 34 shown below were prepared in the same manner as above.

EXAMPLE 25

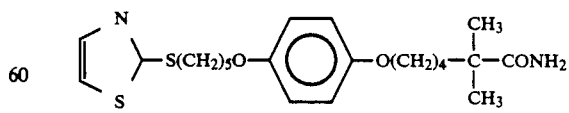

Ethyl 6-[p-[5-[2-(4,5-dihydro)thiazolylthio]pentyloxy]phenoxy]-2,2-dimethylhexanoate

Physicochemical Properties (1) Oil
(2) NMR spectrum (CDCl$_3$)

δ: 1.16 (6H, s), 1.20 (3H, t), 1.32–2.00 (12H, m), 3.10 (2H, t), 3.36 (2H, t), 3.64–4.00 (4H, m), 4.00–4.32 (4H, m), 6.78 (4H, s)
(3) IR spectrum (cm⁻¹)
1715, 1220

EXAMPLE 26

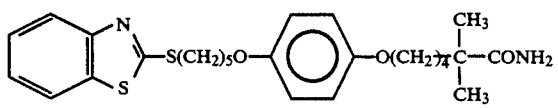

Ethyl 6-[p-[5-(2-benzothiazolylthio)pentyloxy]phenoxy]-2,2-dimethylhexanoate

Physicochemical Properties (1) Oil
(2) NMR spectrum (CDCl₃)
δ: 1.16 (6H, s), 1.20 (3H, t), 1.32–2.08 (12H, m), 3.36 (2H, t), 3.76–4.00 (4H, m), 4.10 (2H, q), 4.78 (4H, s), 7.14–7.50 (2H, m), 7.64–7.82 (2H, m)
(3) IR spectrum (cm⁻¹)
1715, 1220

EXAMPLE 27

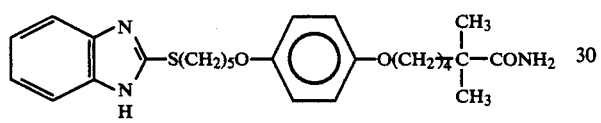

Ethyl 6-[p-[5-(2-benzimidazolylthio)pentyloxy]phenoxy]-2,2-dimethylhexanoate

Physicochemical Properties (1) Melting point 54°–56° C.
(2) Elemental analysis (C₂₈H₃₈N₂O₄S)

|  | C (%) | H (%) | N (%) |
|---|---|---|---|
| Calcd. | 67.44 | 7.68 | 5.62 |
| Found | 67.59 | 7.43 | 5.81 |

(3) NMR spectrum (CDCl₃)
δ: 1.16 (6H, s), 1.24 (3H, t), 4.10 (2H, q), 6.74 (4H, s)

EXAMPLE 28

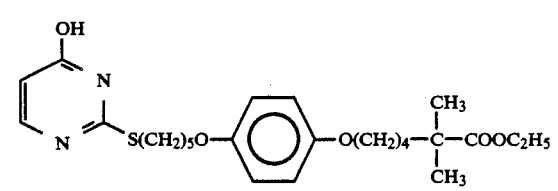

Ethyl 6-[p-[5-(4-hydroxy-2-pyrimidylthio)pentyloxy]-2,2-dimethylhexanoate

Physicochemical Properties (1) Melting point 81°–82° C.
(2) NMR spectrum (CDCl₃)
δ: 1.18 (6H, s), 1.24 (3H, t), 1.32–2.00 (12H, m), 3.22 (2H, t), 3.76–4.00 (4H, m), 4.12 (2H, q), 6.22 (1H, d), 6.80 (4H, s), 7.84 (1H, d)
(2) IR spectrum (cm⁻¹)
1720, 1650, 1220

EXAMPLE 29

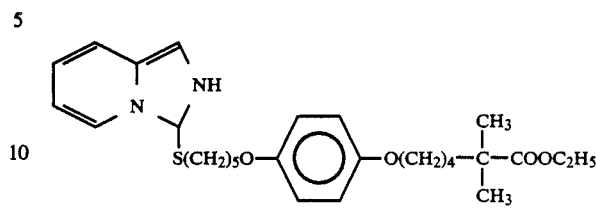

Ethyl 6-[p-[5-(4-hydroxy-2-pyrimidylthio)pentyloxy]phenoxy]-2,2-dimethylhexanoate Physicochemical Properties (1) NMR spectrum (CDCl₃)
δ: 1 16 (6H, s), 1.22 (3H, t), 1.32–2.00 (12H, m), 2.96 (2H, t), 3.72–4.00 (4H, m), 4.10 (2H, q), 6.50–6.86 (6H, m), 7.32–7.36 (2H, m), 8.06–8.24 (1H, m)
(3) IR spectrum (cm⁻¹)
1715, 1225

EXAMPLE 30

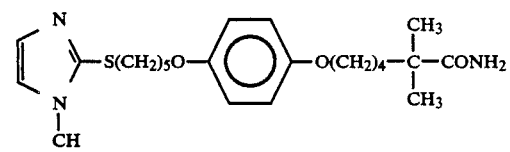

6-[p-[5-(1-Methyl-2-imidazolylthio)pentyloxy]phenoxy]-2,2-dimethylhexanamide

Physicochemical Properties (1) Melting point 86°–88° C.
(2) NMR spectrum (CDCl₃)
δ: 1.20 (6H, s), 1.32–1.96 (12H, m), 3.06 (2H, t), 3.88 (4H, t), 6.78 (4H, s), 6.90 (1H, d), 7.04 (1H, d)
(3) IR spectrum (cm⁻¹)
1640, 1610, 1220

EXAMPLE 31

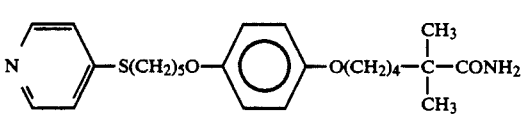

6-[p-[5-(4-Pyridylthio)pentyloxy]phenoxy]-2,2-dimethylhexanamide

Physicochemical Properties (1) Melting point 100°–102° C.
(2) NMR spectrum (CDCl₃)
δ: 1.20 (6H, s), 1.32–2.04 (12H, m), 3.00 (2H, t), 3.90 (2H, t), 3.92 (2H, t), 6.80 (4H, s), 7.10 (2H, dd), 8.38 (2H, dd)
(3) IR spectrum (cm⁻¹)
1640, 1610, 1220

EXAMPLE 32

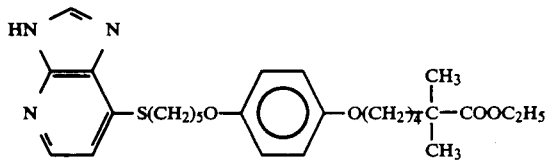

Ethyl 6-[p-[5-(6-purinylthio)pentyloxy]phenoxy]-2,2-dimethylhexanoate

Physicochemical Properties (1) Melting point 83°-85° C.
(2) NMR spectrum (CDCl₃)
  δ: 1.16 (6H, s), 1.22 (3H, t), 1.32–2.04 (12H, m), 3.44 (2H, t), 3.76–4.00 (4H, m), 4.10 (2H, q), 6.80 (4H, s), 8.24 (1H, s), 8.76 (1H, s)
(3) IR spectrum (cm⁻¹)
  1715, 1230

EXAMPLE 33

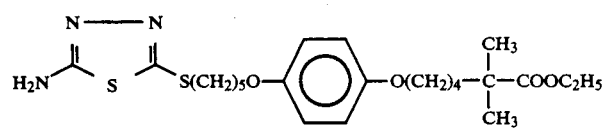

Ethyl 6-[p-[5-(5-amino-1,3,4-thiadiazol-2-ylthio)pentyloxy]phenoxy]-2,2-dimethylhexanoate Physicochemical Properties (1) Melting point 91°-93° C.
(2) NMR spectrum (CDCl₃)
  δ: 1.14 (6H, s), 1.20 (3H, t), 132–2.08 (12H, m), 3.12 (2H, t), 3.88 (4H, t), 4.10 (2H, q), 6.76 (4H, s)
(3) IR spectrum (cm⁻¹)
  20, 1600, 1230

EXAMPLE 34

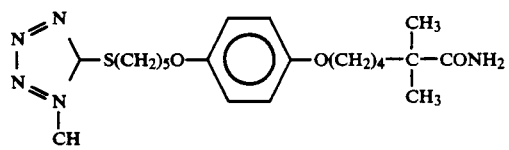

6-[p-[5-(1-Methyl-5-tetrazolylthio)pentyloxy]phenoxy]-2,2-dimethylhexanamide

Physicochemical Properties (1) Melting point 102°-104° C.
(2) NMR spectrum (CDCl₃)
  δ: 1.20 (6H, s), 1.32–2.08 (12H, m), 3.12 (2H, t), 3.38 (2H, t), 3.90 (7H, m), 6.80 (4H, s)
(3) IR spectrum (cm⁻¹)
  1650, 1625, 1230

EXAMPLE 35

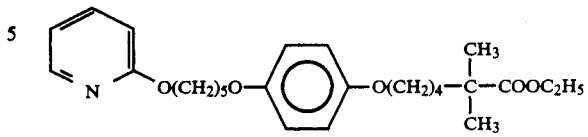

To a mixture of 292 mg 2-hydroxypyridine and 5 ml N,N-diemthylformamide, was added under ice cooling 150 mg of 60% sodium hydride in oil, and the resulting mixture was stirred at room temperature for 15 minutes. The reaction mixture was again cooled in ice, 1.2 g ethyl 6-[p-(5-bromopentyloxy)phenoxy]-2,2-dimethylhexanoate was added, and the mixture was stirred at room temperature for 12 hours. The solvent was distilled off under reduced pressure, the residue was extracted with chloroform, and the extract was washed with water and worked up as usual. The crude product thus obtained was purified by silica gel column chromatography (chloroform), affording 495 mg ethyl 6-[p-[5-(2-pyridyloxy)pentyloxy]phenoxy]-2,2-dimethylhexanoate as oil.

Physicochemical Properties (1) NMR spectrum (CDCl₃)
  δ1.16 (6H, s), 4.10 (2H, q), 6.52 (1H, dd), 1.22 (3H, t), 6.10 (1H, d), 6.76 (4H, s)
(2) IR spectrum (cm⁻¹)
  1726, 1660, 1594, 1510, 1230

Compounds of Examples 36 through 41 shown below were prepared in the same manner as above.

Example 36

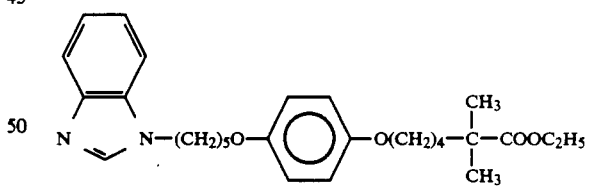

Ethyl 6-[p-[5-(1-benzimidazolyl)pentyloxy]phenoxy]-2,2-dimethylhexanoate

Physicochemical Properties (1) Melting point 52°-55° C.
(2) Elemental analysis ($C_{28}H_{38}N_2O_4$)

|        | C (%) | H (%) | N (%) |
| ------ | ----- | ----- | ----- |
| Calcd. | 72.07 | 8.21  | 6.00  |
| Found  | 72.25 | 8.40  | 6.18  |

(3) NMR spectrum (CDCl₃)
  δ: 1.16 (6H, s), 1.20 (3H, t), 6.76 (4H, s)
(2) IR spectrum (cm⁻¹)

1724, 1512, 1246, 1232, 1218, 1152

Example 37

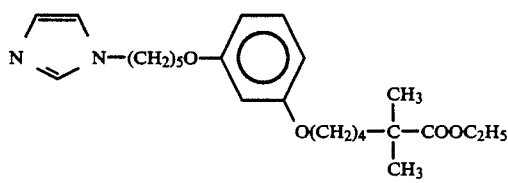

Ethyl 6-[m-[5-(1-imidazolyl)pentyloxy]phenoxy]-2,2-dimethylhexanoate

Physicochemical Properties (1) NMR spectrum (CDCl₃)
  δ: 1.18 (6H, s), 7.44 (1H, s), 1.24 (3H, t), 4.10 (2H, q)
(2) IR spectrum (cm⁻¹)
  1720, 1590, 1280, 1180

Example 38

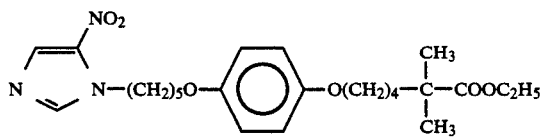

Ethyl 6-[p-[5-(2-nitro-1-imidazolyl)pentyloxy]phenoxy]-2,2-dimethylhexanoate

Physicochemical Properties (1) Melting point 53°–55° C.
(2) NMR spectrum (CDCl₃)
  δ: 1.20 (6H, s), 1.24 (3H, t), 1.32–2.12 (12H, m), 3.72–4.24 (8H, m), 6.82 (4H, s), 7.42 (1H, d), 7.78 (1H, d)
(3) IR spectrum (cm⁻¹)
  1715, 1215

Example 39

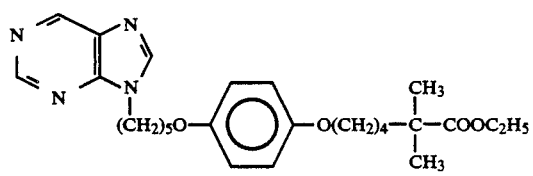

Ethyl 6-[p-[5-(7H-imidazo[4,5-d]pyrimidin-1-yl)pentyloxy]phenoxy]-2,2-dimethylhexanoate

Physicochemical Properties (1) NMR spectrum (CDCl₃)
  δ: 1.20 (6H, s), 1.24 (3H, t), 1.36–2.24 (12H, m), 3.90 (2H, t), 3.92 (2H, t), 4.12 (2H, q), 4.34 (2H, t), 6.82 (4H, s), 8.12 (1H, s), 9.00 (1H, s), 9.16 (1H, s)
(2) IR spectrum (cm⁻¹)
  1710, 1655, 1220

EXAMPLE 40

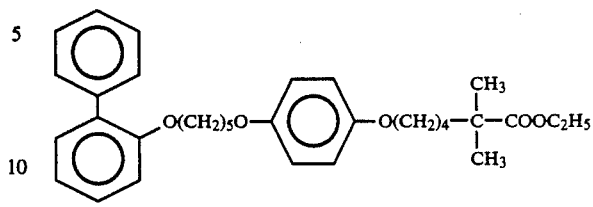

Ethyl 6-[p-[5-(2-biphenyloxy)pentyloxy]phenoxy]-2,2-dimethylhexanoate

Physicochemical Properties (1) NMR spectrum (CDCl₃)
  δ: 1.18 (6H, s), 1.22 (3H, t), 1.36–1.96 (12H, m), 3.70–4.06 (6H, m), 4.10 (2H, q), 6.80 (4H, s), 6.86–7.64 (9H, m)
(2) IR spectrum (cm⁻¹)
  1720, 1225

Example 41

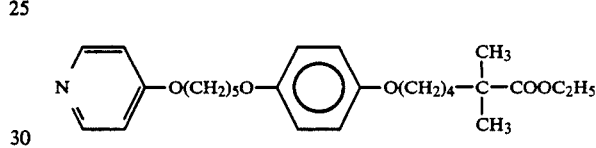

Ethyl 6-[p-[5-(4-pyridyloxy)pentyloxy]phenoxy]-2,2-dimethylhexanoate

Physicochemical Properties (1) NMR spectrum (CDCl₃)
  δ: 1.16 (6H, s), 1.22 (3H, t), 1.32–2.04 (12H, m), 3.60–4.00 (6H, m), 4.10 (2H, q), 6.36 (2H, dd.), 6.80 (4H, s), 7.24 (2H, dd)
(2) IR spectrum (cm⁻¹)
  1715, 1630, 1210

Reference Example 5

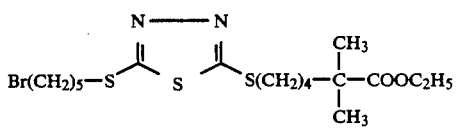

To a mixture of 5 g ethyl 6-(5-mercapto-1,3,4-thiazol-2-ylthio)-2,2-dimethylhexanoate and 10 ml N,N-dimethyl formamide, were added 3.6 g 1,5-dibromopentane and 2.6 g potassium carbonate, and the resulting mixture was stirred at room temperature for 12 hours. The solvent was distilled off under reduced pressure, the residue was extracted with chloroform, and the extract was worked up as usual. The crude product thus obtained was purified by silica gel column chromatography (chloroform), affording 2.7 g ethyl 6-[2-(5-bromopenylthio)-1,3,4-thiadiazol-5-ylthio]-2,2-dimethylhexanoate as oil.

Physicochemical Properties (1) NMR spectrum (CDCl₃)
  δ: 1.16 (6H, s), 4.12 (2H, q), 12.4 (3H, t)
(2) IR spectrum (cm⁻¹)
  2980, 1728, 1388

Example 42

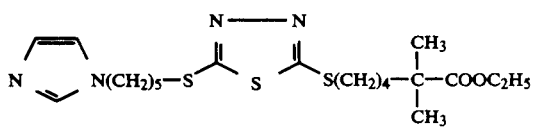

To a mixture of 390 mg imidazole and 10 ml anhydrous N,N-dimethylformamide, were added under ice cooling 230 mg of 60% sodium amide in oil, and the resulting mixture was stirred at room temperature for 15 minutes. Ethyl 6-[2-(5-bromopentylthio) -1,3,4-thiadiazol-5-ylthio]-2,2-dimethylhexanoate (2.7 g) obtained in Reference Example 5, was added, and the mixture was heated at 60° to 70° C. with stirring for two hours. The solvent was distilled off under reduced pressure, the residue was worked up as usual, and the crude product thus obtained was purified by silica gel column chromatography,), affording 1.6 g ethyl 6-[2-[5-(1-imidazolyl)pentylthio)-1,3,4-thiadiazol-5-ylthio]-2,2-dimethylhexanoate as oil.

Physicochemical Properties (1) NMR spectrum (CDCl$_3$)
  δ: 1.14 (6H, s), 4.10 (2H, q), 12.2 (3H, t), 7.44 (1H, s), 3.94 (2H, t)
(2) IR spectrum (cm$^{-1}$)
  1730, 1508, 1400, 1230, 1146

Example 43

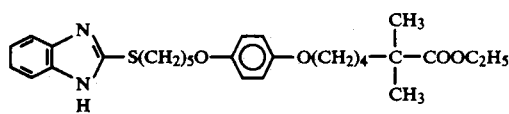

To a mixture of 570 mg 2-mercapto-1H-imidazo[4,5-b]-pyridine and 18 ml methanol, was added a mixture of 166 mg sodium hydroxide, 6 ml water and 1.8 g ethyl 6-[p-(5-bromopentyloxy)phenoxy]-2,2-dimethylhexanoate. The resulting mixture was heated under reflux for 12 hours, the solvent was distilled off under reduced pressure, and the residue was purified by silica gel column chromatography, affording 610 mg ethyl 6-[p-[5-(1H-imidazo[4,5-b]pyridin-2-ylthio)pentyloxy]phenoxy]-2,2-dimethylhexanoate as waxy solid.

Physicochemical Properties (1) NMR spectrum (CDCl$_3$)
  δ: 1.16 (6H, s), 6.76 (4H, s), 1.20 (3H, t), 8.28 (1H, dd), 4.08 (2H,q)
(2) IR spectrum (cm$^{-1}$)
  1726, 138, 1038

Compound of Example 44 shown below was prepared in the same manner as above

Example 44

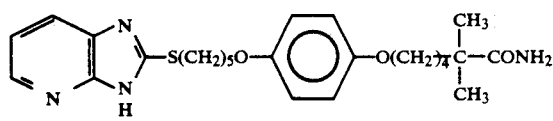

6-[p-[5-(1H-Imidazo[4,5-b]pyridin-2-ylthio)pentyloxy]-phenoxy]-2,2-dimethylhexanamide

Physicochemical Properties (1) Melting point 105°–107° C.
(2) NMR spectrum (CDCl$_3$)
  δ: 1.20 (6H, s), 1.32–2.08 (12H, m), 3.42 (2H, t), 3.90 (4H, t), 6.76 (4H, s), 7.16 (1H, d), 7.82 (1H, d), 8.26 (1H, dd)
(2) IR spectrum (cm$^{-1}$)
  1640, 1610, 1220

Example 45

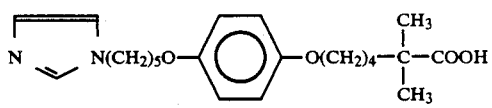

To a solution of 3 g ethyl 6-[p-[5-(1-imidazolyl)pentyloxy]phenoxy]-2,2-dimethylhexanoate in 15 ml methanol, was added a solution of 580 mg sodium hydroxide in 6 ml water, and the mixture was heated under reflux for 5 hours. Methanol was distilled off under reduced pressure, and dilute hydrochloric acid was added to the remaining aqueous soluiton to lower its pH down to about 5. The solid which separated out was collected by filtration, washed with water, and recrystallized from methanol, affording 2.3 g of 6-[p-[5-(1-imidazolyl)pentyloxy]phenoxy]-2,2-dimethylhexanoic acid.

Physicochemical Properties (1) Melting point 118°–119° C.
(2) Elemental analysis (C$_{22}$H$_{32}$N$_2$O$_4$)

|  | C (%) | H (%) | N (%) |
|---|---|---|---|
| Calcd. | 68.01 | 8.30 | 7.21 |
| Found | 67.98 | 8.52 | 7.11 |

Example 46

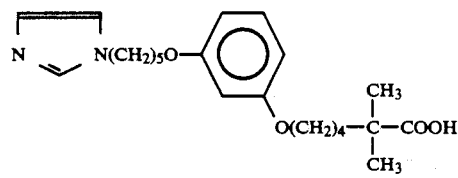

A mixture of 3.5 g ethyl 6-[m-[5-(1-imidazolyl)pentyloxy]phenoxy]-2,2-dimethylhexanoate, 20 ml of 1N NaOH solution and 20 ml ethanol was heated under reflux overnight. Ethanol was distilled off under reduced pressure, and concentrated hydrochloric acid was added to the remaining aqueous soluiton to lower its pH down to about 4.0. The pasty solid which separated out was extracted with chloroform, and the extract was washed with water and dried. The solvent was ditilled off, and the crude product thus obtained was purified by silica gel column chromatography, affording 3.2 g of 6-[m-[5-(1-imidazolyl)pentyloxy]-phenoxy]-2,2-dimethylhexanoic acid.

Physicochemical Properties (1) Liquid
(2) NMR spectrum (CDCl$_3$)

δ: 1.20 (6H, s), 1.32-2.10 (12H, m), 3.76-4.16 (6H, m), 6.30-6.56 (3H, m), 6.92 (1H, s), 7.00-7.28 (2H, md), 7.88 (1H, s)

(3) IR spectrum (cm$^{-1}$)
1710, 1610, 1600, 1190

Example 47

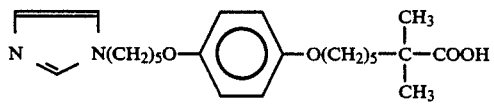

To a solution of 2.5 g ethyl 6-[p-[5-(1-imidazolyl)pentyloxy]phenoxy]hexanoate in 10 ml methanol, was added a solution of 520 mg sodium hydroxide in 5 ml water, and the mixture was heated under reflux for 5 hours. Methanol was distilled off under reduced pressure, and dilute hydrochloric acid was added to the remaining aqueous soluiton to lower its pH down to about 5. The solid which separated out was collected by filtration, washed with water, and recrystallized from methanol, affording 2 g of 6-[p-[5-(1-imidazolyl)pentyloxy]phenoxy]hexanoic acid.

Physicochemical Properties (1) Melting point 148°-150° C.
(2) Elemental analysis ($C_{20}H_{28}N_2O_4$)

|        | C (%) | H (%) | N (%) |
|--------|-------|-------|-------|
| Calcd. | 66.64 | 7.83  | 7.77  |
| Found  | 6.428 | 7.98  | 7.58  |

Example 48

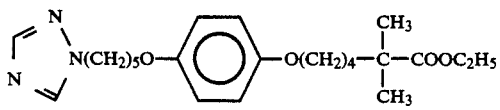

To a solution of 2.16 g ethyl 6-[p-(5-bromopentyloxy]-phenoxy)-2,2-dimethylhexanoate in 10 ml DMF, was added with stirring 0.55 g sodium salt of 1,2,4-triazole at room temperature, and stiring was continued overnight. DMF was distilled off under reduced pressure, the residue was extracted with chloroform, and the extract was washed with water, dried and concentrated. The crude product thus obtained was purified by silica gel column chromatography, affording 1.21 g of ethyl 6-[p-[5-(1,2,4-triazol-1-yl)pentyloxy]phenoxy]-2,2-dimethylhexanoate.

Physicochemical Properties (1) Melting point 51°-53° C.
H (2) NMR spectrum (CDCl$_3$)

δ: 1.14 (6H, s), 1.20 (3H, t), 1.32-2.10 (12H, m), 3.86 (4H, t), 3.92-4.30 (4H, m), 6.78 (4H, s), 7.92 (1H, s), 8.02 (1H, s)

(3) IR spectrum (cm$^{-1}$)
1715, 1210

Example 49

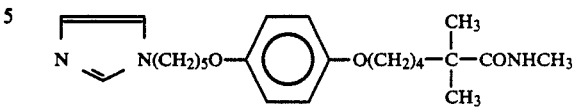

A mixture of 1 g 6-[p-[5-(1-imidazolyl)pentyloxy]-phenoxy]-2,2-dimethylhexanoic acid and 10 ml thionyl chloride was heated under reflux for one hour, excess thionyl chloride was distilled off under reduced pressure, and the acid chloride thus formed was dissolved in 5 ml benzene. This solution was added under ice cooling to a mixture of 870 mg methylamine hydrochloride, 1.6.g triethylamine and 10 ml dry benzene, and the resulting mixture was stirred at room temperature for 12 hours. The solvent was distilled off under reduced pressure, the residue was extracted with chloroform, and the extract was washed with water, dried over anhydrous magnesium sulfate and concentrated. The concentrate was then subjected to column chromatography (chloroform/methanol =98/2 ), and the solid thus obtained was recrystallized from ethyl acetate, affording 580 mg of 6-[p-[5-(1-imidazolyl)pentyloxy]phenoxy]-2,2-dimethylhexanoic acid methylamide.

Physicochemical Properties (1) Melting point 92°-94° C.
(2) Elemental analysis ($C_{23}H_{35}N_3O_3$)

|        | C (%) | H (%) | N (%) |
|--------|-------|-------|-------|
| Calcd. | 68.80 | 8.79  | 10.46 |
| Found  | 68.56 | 8.86  | 10.81 |

(3) NMR spectrum (CDCl$_3$)
δ: 1.16 (6H, s), 6.80 (4H, s), 2.78 (3H, s),

Example 50

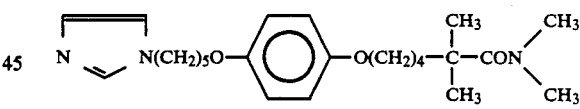

6-[p-[5-(1-Imidazolyl)pentyloxy]phenoxy]-2,2-dimethylhexanoic acid dimethylamide Physicochemical Properties (1) NMR spectrum (CDCl$_3$)
δ: 1.24 (6H, s), 3.00 (6H, s), 6.78 (4H, s), 7.46 (1H, s)
(2) IR spectrum (cm$^{-1}$)
1624, 1508, 1394, 1230

Example 51

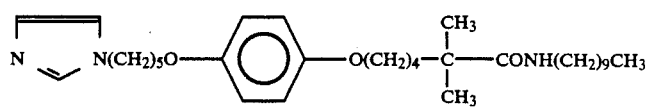

6-[p-[5-(1-Imidazolyl)pentyloxy]phenoxy]-2,2-dimethylhexanoic acid decylamide

Physicochemical Properties (1) Melting point 61°–63° C.
(2) Elemental analysis ($C_{32}H_{53}N_3O_3$)

|  | C (%) | H (%) | N (%) |
|---|---|---|---|
| Calcd. | 72.82 | 10.12 | 7.96 |
| Found | 72.69 | 10.09 | 7.88 |

(3) NMR spectrum (CDCl₃)
δ: 0.88 (3H, t), 1.16 (6H, s), 6.80 (4H, s), 7.46 (1H, s)

Example 52

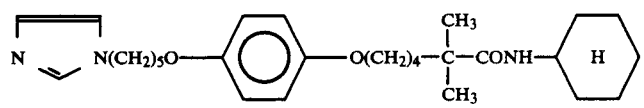

6-[p-[5-(1-Imidazolyl)pentyloxy]phenoxy ]-2,2-dimethylhexanoic acid cyclohexylamide

Physicochemical Properties (1) Melting point 102°–104° C.
(2) Elemental analysis ($C_{28}H_{43}N_3O_3$)

|  | C (%) | H (%) | N (%) |
|---|---|---|---|
| Calcd. | 71.61 | 9.23 | 8.95 |
| Found | 71.82 | 9.12 | 8.78 |

(3) NMR spectrum (CDCl₃)
δ: 1.16 (6H, s), 6.78 (4H, s), 7.48 (1H, s)

Example 53

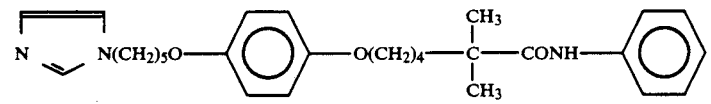

6-[p-[5-(1-Imidazolyl)pentyloxy]phenoxy]-2,2-dimethylhexanoic acid anilide

Physicochemical Properties (1) Melting point 63°–65° C.
(2) Elemental analysis ($C_{28}H_{37}N_3O_3$)

|  | C (%) | H (%) | N (%) |
|---|---|---|---|
| Calcd. | 72.54 | 8.04 | 9.06 |
| Found | 72.75 | 8.21 | 9.32 |

(3) NMR spectrum (CDCl₃)
δ: 1.32 (6H, s), 6.80 (4H, s)

Example 54

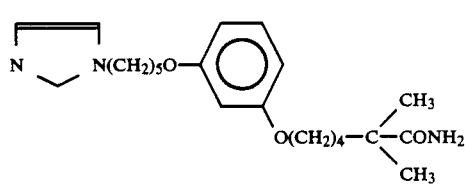

6-[m-[5-(1-Imidazolyl)pentyloxy]phenoxy]-2,2-dimethylhexanamide

Physicochemical Properties (1) Pasty solid
(2) NMR spectrum (CDCl₃)
δ: 1.20 (6H, s), 1.30–2.08 (12H, m), 3.76–4.16 (6H, m), 6.42 (2H, m), 6.54 (1H, dd), 6.92 (1H, s), 7.04 (1H, s), 7.46 (1H, d), 7.72 (1H, dd)
(3) IR spectrum (cm⁻¹)
1665, 1600, 1190

Example 55

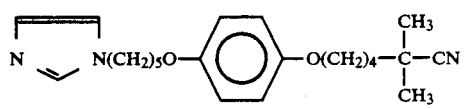

To a solution of 0.97 g 6-[p-[5-(1-imidazolyl)pentyloxy]phenoxy]-2,2-dimethylhexanamide in 50 ml dichloromethane was added 0.94 ml pyridine, the solution was cooled down to −20° C., 1.57 g phosphorus pentachloride was added, and the resulting mixture was stirred to allow the temperature to rise to 15° C. over a period of about one hour. Chloroform (30 ml) and ice water (30 ml) were admixed in that order, and the organic layer was collected and washed with 5% aqueous solution of sodium bicarbonate until the pH of aqueous layer rose to 7.5 to 8.0 and then with saturated sodium chloride solution. After dehydration, the solvent was distilled off, and the residue was purified by silica gel column chromatography, affording 0.82 g of 6-[p-[5-(1-imidazolyl) pentyloxy]phenoxy]-2,2-dimethylhexane-nitrile.

Physicochemical Properties (1) Melting point 61°–63° C.
(2) NMR spectrum (CDCl₃)
δ: 1.34 (6H, s), 1.44–2.08 (12H, m), 3.76–4.08 (6H, m), 6.80 (1H, s), 7.04 (1H, s), 7.46 (1H, s)
(3) IR spectrum (cm⁻¹)
2220, 1230

Example 56

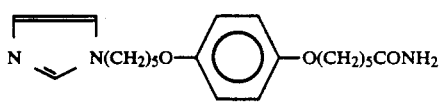

A mixture of 2 g 6-[p-[5-(1-imidazolyl)pentyloxy]phenoxy]hexanoic acid and 15 ml thionyl chloride was heated at 80° C. for one hour. After distilling off excess thionyl chloride under reduced pressure, the residue was dissolved in 50 ml anhydrous benzene, ammonia gas was introduced into the benzene solution for 30 minutes under ice cooling, and the solvent was distilled off under reduced pressure. Water was added to the residue, and the solid which separated out was collected by filtration and recrystallized from ethanol, affording 1.6 g of 6-[p-[5-(1-imidazolyl)pentyloxy]phenoxy]-2,2-dimethylhexanamide.

Physicochemical Properties (1) Melting point 101°-110° C.
(2) Elemental analysis ($C_{20}H_{29}N_3O_3$)

|  | C (%) | H (%) | N (%) |
|---|---|---|---|
| Calcd. | 66.83 | 8.13 | 11.69 |
| Found | 66.79 | 8.21 | 11.82 |

(3) NMR spectrum ($CDCl_3$)
:6.80 (4H, s), 7.04 (1H, s), 6.90 (1H, s), 7.45 (1H, s)

Example 57

(Compound 1→Compound 2)

A mixture of 24.2 g of compound 1, 30.4 g of powdery potassium carbonate, 55.3 g ethyl 6-bromo-2,2-diemthylhexanoate (YBE) and 300 ml ethanol was heated under reflux with stirring for 2.5 hours. After cooling the reaction mixture, the solid which separated out was filtered off, the filtrate was concentrated to dryness under reduced pressure, the residue was extracted with 300 ml toluene, and the extract was washed with water, dried and concentrated. The crude product thus obtained was purified by silica gel column chromatography, the chloroform eluate was collected, the solvent was removed by distillation, and the residue was dried in vacuum, giving 52.7 g of compound 2.

(Compound 2→Compound 3)

A mixture of 22.4 g of compound 2, 12.0 g of powdery potassium carbonate, 73.6 g 1,5-dibromopentane (DBP) and 80 ml methyl ethyl ketone was heated under reflux overnight with stirring. After cooling the reaction mixture, the solid which separated out was filtered off, the filtrate was concentrated to dryness, and the residue was extracted with 100 ml toluene. The extract was washed with an aqueous solution of sodium chloride, toluene was distilled off under reduced pressure, and excess DBP was removed by distillation at a bath temperature of 90° C. under a pressure of 1 to 0.5 mm/Hg, affording 27.9 g of compound 3.

(Compound 3→Compound A)

A mixture of 17.2 g of compound 3, 22.0 g imidazole and 100 ml ethyl acetate was heated under reflux for five hours with stirring. The reaction mixture was cooled and dried, ethyl acetate was removed by distillation, and the residue was purified by silica gel column chromatography. The eluate in (5:95) methanol/chloroform was collected, the solvents were distilled off, and the residue was dried under reduced pressure, affording 10.5 of compound A.

(Compound A→Compound B)

A mixture of 8.7 g of compound A, 60 ml 5%-NaOH and 80 ml ethanol was gently heated under reflux overnight with stirring. After cooling, ethanol was distilled off under reduced pressure, concentrated hydrochloric acid was added to lower the pH to 1.5, and the resulting mixture was extracted with 150 ml chloroform. The extract was washed with water and dried, and the solvent was distilled off, giving 8.0 g of compound B.

Example 58

(Compound 4→Compound 5)

To a mixture of 10.1 g of compound 4, 12.4 g of powdery potassium carbonate and 100 ml DMF, was added dropwise YBE with stirring under ice cooling over a period of about one hour. Stirring under ice cooling was continued for an additional one hour, and the reaction mixture was kept at room temperature overnight with stirring. The solid which separated out was filtered off, DMF was distiled off under reduced pressure, the residue was extracted with 150 ml ethyl acetate, and the extract was washed with water, dried and concentrated. The crude product thus obtained was purified by silica gel column chromatography, the chloroform eluate was collected, and the solvent was removed by distillation, giving 16.7 g of compound 5.

(Compound 5→Compound 6)

A mixture of 14.8 g of compound 5, 9.0 g of powdery potassium carbonate, 46.0 g DBP and 60 ml methyl ethyl ketone was heated under reflux overnight with stirring. After cooling the reaction mixture, the solid which separated out was filtered off, methyl ethyl ketone was distilled off under reduced pressure, and the residue was extracted with 100 ml chloroform. The extract was washed with water, dried and treated in the same way as in the step of Compound 2→Compound 3 in Example 57. The chloroform eluate from silica gel column chromatography was collected, and 21.1 g of compound 6 was obtained by distilling off chloroform from the eluate.

(Compound 6→Compound C)

A mixture of 13.4 g of compound 6, 16.3 g imidazole and 80 ml ethyl acetate was heated under reflux for five hours with stirring. The reaction mixture was worked up in the same manner as in the step of Compound 3→Compound A in Example 57, and 8.1 g of compound C was obtained from the chloroform eluate.

(Compound C→Compound D)

To a solution of 1.8 g of compound C in 25 ml dichloromethane, was added with stirring and under ice cooling 1.0 g m-CPBA over a period of one hour. Stirring under ice cooling was continued for an additional one hour, followed by stirring at room temperature overnight. The reaction mixture was washed with an aqueous solution of sodium bicarbonate and then with water, the organic layer was dried and concentrated, and the crude product thus obtained was purified by silica gel column chromatography, affording 1.7 g of compound D from the eluate in (5:95) methanol/chloroform.

Example 59

(Compound 7→Compound 8)

To a mixture of 10.2 g of compound 7, 12.4 g of powdery potassium carbonate and 100 ml DMF, was added dropwise YBE with stirring over a period of about one hour. Stirring was continued at room temperature overnight and then at 55° C. for six hours. The solid which separated out was filtered off, DMF was distilled off under reduced pressure, the residue was worked up in the same manner as in the step of Compound 4→Compound 5 in Example 58. Compound 8 (13.5 g) was obtained from the chloroform eluate of silica gel column chromatography.

(Compound 8→Compound 9)

A mixture of 11.9 g of compound 8, 7.2 g of powdery potassium carbonate, 36.8 g DBP and 75 ml methyl ethyl ketone was heated under reflux for six hours with stirring. The reaction mixture was worked up in the same manner as in the step of Compound 5→Compound 6 in Example 58, and 14.0 g of compound 9 was obtained from the chloroform eluate of silica gel column chromatography.

(Compound 9→Compound E)

A mixture of 6.9 g of compound 9, 8.5 g imidazole and 50 ml ethyl acetate was heated under reflux for five hours with stirring. The reaction mixture was worked up in the same manner as in the steps of Compound 3→Compound A in Example 57, and 5.9 g of compound E was obtained from the chloroform eluate.

(Compound E→Compound F)

To a solution of 1.8 g of compound E in 25 ml dichloromethane, was added with stirring and under ice cooling 1.0 g m-CPBA over a period of one hour. The reaction mixture was worked up in the same manner as in the step of Compound C →Compound D in Example 58, and 1.5 g of compound F was obtained from the eluate in (5:95) methanol/chloroform.

Example 60

(Compound 10→Compound 11)

To a mixture of 50.2 g of compound 10, 8.7 g of powdery potassium carbonate and 450 ml DMF, was added dropwise 14.1 g YBE with stirring at 75° C. over a period of six hours. Stirring at that temperature was further continued overnight, the solid which separated out was filtered off, DMF was distilled off under reduced pressure, and the residue was extracted with 600 ml ethyl acetate. The extract was washed with water, the organic layer was collected and dried, the solvent was distilled off, and the residue was vacuum-dried, giving 10.1 g of compound 11.

( Compound 11→Compound 12 )

A mixture of 10.0 g of compound 11, 6.3 g of powdery potassium carbonate, 32.2 g DBP and 50 ml methyl ethyl ketone was heated under reflux for eight hours with stirring, and the reaction mixture was worked up in the same manner as in the step of Compound 2→Compound 3 in Example 57. The chloroform eluate of silica gel column chromatography was collected, and the solvent was distilled off from the eluate, giving 12.0 g of compound 12.

(Compound 12→Compound G)

A mixture of 6.5 g of compound 12, 8.2 g imidazole and 50 ml ethyl acetate was heated under reflux for 3.5 hours with stirring. The reaction mixture was worked up in the same manner as in the step of Compound 3→Compound A in Example 57, and 2.3 g of compound G was obtained from the ( 5:95 ) methanol/chloroform eluate.

Ex. 61

According to the same procedure as in Example 49, 6 -[5-(1-imidazolyl)pentyloxy]phenoxy]-2,2-dimethyl-hexaneheptylamide of the following formula was obtained.

Melting point: 61°-63° C.
Elemental analysis for $C_{29}H_{47}N_3O_3$

|  | C (%) | H (%) | N (%) |
|---|---|---|---|
| Calculated | 71.71 | 9.75 | 8.65 |
| Found | 71.58 | 9.72 | 8.79 |

NMR spectrum (CDCl$_3$)
δ: 0.88 (3H, t), 6.82 (4H, s) 1.20 (6H, s)
Compound I: o--hydroxyphenol;

Compound 2: 6-[o-(hydroxy)phenoxy]-2,2-dimethyl-hexanoic acid ethyl ester:

NMR spectrum (CDCl$_3$):
δ: 1.16(6H, s), 1.24(3H, t), 1.36–2.00(6H, m), 3.88–4.12(2H, m), 4.14(2H q), 6.72–7.00(4H,m)
IR spectrum(cm$^{-1}$) 1735
Compound 3:
6-[o-(5-bromopentyloxy)phenoxy]-2,2-dimethylhexanoic acid ethyl ester NMR spectrum (CDCl$_3$):
δ: 1.18 (6H, s), 1.24 (3H, t), 1.32–2.12 (12 H, m), 3.34 –3.56 (2H, m), 3.88–4.12 (4H, m), 4.12 (2H, q), 6.88 (4H, s)
IR spectrum (cm$^{-1}$): 1735
Compound A:
6-(o-[5-(1-imidazolyl)pentyloxy]phenoxy]-2,2-dimethylhexanoic acid ethyl ester
NMR spectrum (CDCl$_3$):
δ: 1.20 (6H, s), 1.26 (3H, t), 1.32–2 08(12H, m), 3.90–4.10 (6H, m), 4.14 (2H, q), 6.92 (4H, s), 6.94 (1H, s), 7.08 (1H, s), 7.50 (1H, s) spectrum (cm$^{-1}$) 1750
Compound B:

6-[o-[5-(1-imidazolyl)pentyloxy]phenoxy]-2,2-dimethyl-hexanoic acid

41

NMR spectrum (CDCl$_3$):

δ: 1.18 (6H, s), 1.30–2.08 (12H, m), 3.80–4.20 (6H, m), 6.86 (4H, s), 6.98 (1H, s), 7.16 (1H, s), 8.26 (1H, s)

IR spectrum (cm$^{-1}$): 1740

Compound 5

6-[p-(hydroxy)thiophenoxy]-2,2-dimethylhexanoic acid ethyl ester

NMR spectrum (CDCl$_3$):

δ: 1.14 (6H, s), 1.24 (3H, t), 1.30–1.80 (6H, m), 2.64–2.92 (2H, m), 4.12 (2H, q), 6.78 (2H, d), 7.30 (2H, d)

IR spectrum (cm$^{-1}$) 1745, 1715

Compound 6:

6-[p-(5-bromopentyloxy)thiophenoxy]-2,2-dimethylhexanoic acid ethyl ester

NMR sepctrum (CDCl$_3$):

δ: 1.16 (6H, s), 1.24 (3H, t), 1.32–2.08 (12H, m), 2.64–2 92 (2H, m), 3.30–3.54 (2H, m), 3.84–4.08 (2H, m), 4.12 (2H, q), 6.82 (2H, d), 7.34 (2H, d)

IR Spectrum (cm$^{-1}$): 1740

Compound C:

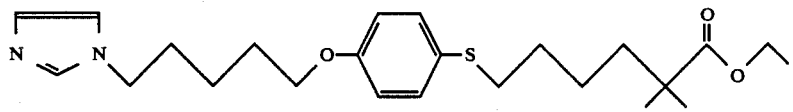

6-[p-[5-(1-imidazolyl)pentyloxy]thiophenoxy]-2,2-dimethylhexanoic acid ethyl ester NMR spectrum (CDCl$_3$):

δ: 1.16 (6H, s), 1.24 (3H, t), 1.32–2.04 (12 H, m), 2.64–2 92 (2H, m), 3.80–4.08 (4H, m), 4.10 (2H, q), 6.80 (2H, d), 6.92 (1H, s), 7.08 (1H, s), 7.32 (2H, d), 7.48 (1H, s)

IR spectrum (cm$^{-1}$) 1730

Compound D:

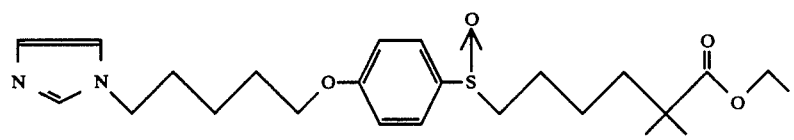

6-[p-[5-(1-imidazolyl)pentyloxy]thiophenoxy]-2,2-dimethylhexanoic acid ethyl ester s-oxide NMR spectrum (CDCl$_3$):

1.16 (6H, s), 1.24 (3H, t), 1.36–2.08 (12H, m), 2.68–2.96 (2H, m), 3.90–4.16 (4H, m), 4.10 (2H, q), 6.98 (1H, s), 7.02 (2H, d), 7.20 (1H, s), 7.48 (1H, s), 7.58 (2H, d)

42

IR spectrum (cm$^{-1}$) 1725

Mass spectrum (EI, in Beam): 448

Compound 8

6-[2-(4-hydroxy)thiopyrimidyl]-2,2-dimethylhexanoic acid ethyl ester

Melting point: 58°–60° C.

NMR spectrum (CDCl$_3$):

δ: 1.16 (6H, s), 1.24 (3H, t), 1.32–1.92 (6H, m), 3.04–3.32 (2H, m), 4.14 (2H, q), 6.24 (1H, d), 7.88 (1H, d)

IR spectrum (cm$^{-1}$) 1735, 1670

Compound 9

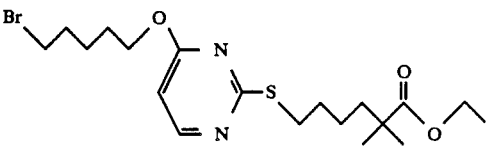

6-[2-[4-(5-bromopentyloxy)]thiopyrimidyl]]-2,2-dimethylhexanoic acid ethyl ester NMR spectrum (CDCl$_3$):

δ: 1.20 (6H, s), 1.26 (3H, t) 1.34–2.10 (12H, m), 3.02–3.22 (2H, m) 3.36–3.54 (2H, m), 4.14 (2H, q), 4.28–4.46 (2H, m), 6.38 (2H, d), 8.22 (2H, d)

IR spectrum (cm$^{-1}$): 1735, 1695

Compound E

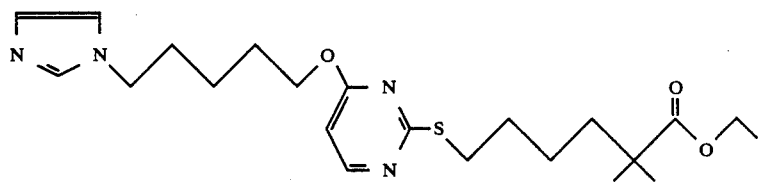

6-[2-[4-[5-(1-imidazolyl)pentyloxy]]thiopyrimidyl]]-2,2-dimethylhexanoic acid ethyl ester NMR spectrum (CDCl$_3$):

δ: 1.96 (6H, s), 1.24 (3H, t), 1.32–2.04 (12H, m), 3.00–3.20 (2H, m), 3.84–4.04 (2H, m), 4.12 (2H, q), 4.24–4.44 (2H, m), 6.34 (1H, d) 6.92 (1H, s), 7.06 (1H, s), 7.48 (1H, s) 8.20 (2H, d)

IR spectrum (cm$^{-1}$): 1735

Compound F

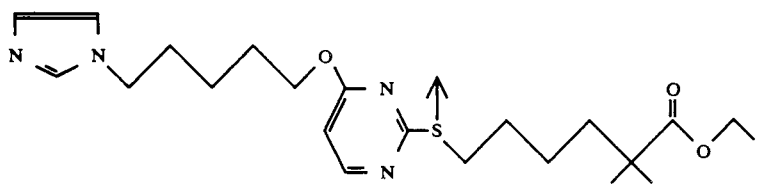

6-[2-[4-[5-(1-imidazolyl)pentyloxy]thiopyrimidyl]]-2,2-dimethylhexanoic acid ethyl ester s-oxide
NMR spectrum (CDCl₃):
δ: 1.16 (6H, s) 1.24 (3H, t), 1.32–2.16 (12H,m) 2.96–3.24 (2H, m), 3.88–4.12 (2H, m), 4.12 (2H, q), 4.32–4.64 (2H, m) 6.76 (1H,d) 6.96 (1H, s) 7.16 (1H, s) 7.74 (1H, s), 8.56 (1H, d)
IR spectrum (cm⁻¹): 1730
Mass spectrum (EI, in Beam): 451
Compound 11

6-[3-[6-(hydroxy)pyridadyloxy]]-2,2-dimethylhexanoic acid ethyl ester
NMR spectrum (CDCl₃)
δ: 1.18 (6H, s), 1.28 (3H, t), 1.32–1.92 (6H, m), 3.92–4.26 (2H, m), 4.14 (2H, q) 6.88–7.12 (2H, m)
IR spectrum (cm⁻¹): 1745, 1690
Compound 12

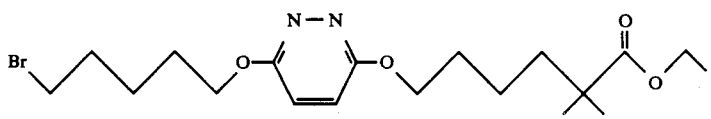

6-[3-[6-(5-bromopentyloxy) pyridadyloxy]]-2 2-dimethylhexanoic acid ethyl ester
NMR spectrum (CDCl₃):
δ: 1.20 (6H,s), 1.24 (3H, t), 1 30–2.08 (12H, m), 3.30–3.50 (2H,m), 3.90–4.24 (4H, m), 4.14 (2H, m), 6.88 (2H, s)
IR spectrum (cm⁻¹): 1740, 1685
Compound G

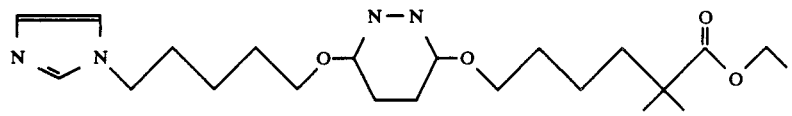

6-[3-[6-[5-(1-imidazolyl)pentyloxy]pyridadyloxy]]-2,2-dimethylhexanoic acid ethyl ester
NMR spectrum (CDCl₃)
δ: 1.18 (6H, s), 1.24 (3H, t), 1.30–2.08 (12H, m), 3.84–4.16 (6H, m), 4.12 (2H, q), 6.90 (2H, s), 6.92 (1H, s), 7.06 (1H, s) 7.46 (1H s)
IR spectrum (cm⁻¹) 1740, 1690

$$A-(CH_2)_l-X^1-(CH_2)_m-X^2-B-X^3-Y-(CH_2)_n-\overset{R_1}{\underset{R_2}{C}}-R_3$$
| Example | A | l | $X^1$ | m | $X^2$ | B | $X^3$ | Y | n | $R_1$ | $R_2$ | $R_3$ |
|---|---|---|---|---|---|---|---|---|---|---|---|---|
| 1 | 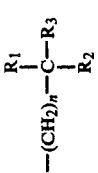 | 0 | — | 5 | —O— |  | —O— | — | 4 | —CH₃ | —CH₃ | —CONH₂ |
| 2 |  | 0 | — | 5 | —O— |  | —O— | — | 4 | —CH₃ | —CH₃ | —CONHCH(CH₃)CH₃ |
| 3 |  | 0 | — | 5 | —O— |  | —O— | — | 4 | —CH₃ | —CH₃ | —CONH—CH₂—C₆H₅ |
| 4 |  | 0 | — | 5 | —O— |  | —O— | — | 4 | —CH₃ | —CH₃ | —CONH₂ |
| 5 |  | 0 | — | 5 | —O— |  | —O— | — | 4 | —CH₃ | —CH₃ | —COOCH₂—C₆H₅ |
| 6 |  | 0 | — | 5 | —O— |  | —O— | — | 4 | —CH₃ | —CH₃ | —COOC(CH₃)₃ |
| 7 | 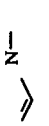 | 0 | — | 5 | —O— |  | —O— | — | 8 | H | H | H |

-continued $$A-(CH_2)_l-X^1-(CH_2)_m-X^2-B-X^3-Y-(CH_2)_n-\overset{R_1}{\underset{R_2}{C}}-R_3$$

| Example | A | l | $X^1$ | m | $X^2$ | B | $X^3$ | Y | n | $R_1$ | $R_2$ | $R_3$ |
|---|---|---|---|---|---|---|---|---|---|---|---|---|
| 8 | imidazole | 0 | — | 5 | —O— | phenyl | —O— | — | 4 | H | H | —COOC$_2$H$_5$ |
| 9 | imidazole | 0 | — | 5 | —O— | phenyl | —O— | — | 5 | H | H | —OH |
| 10 | imidazole | 0 | — | 5 | —O— | phenyl | —O— | — | 0 | H | H | —COOC$_2$H$_5$ |
| 11 | imidazole | 0 | — | 5 | —O— | phenyl | —O— | — | 0 | H | H | H |
| 12 | imidazole | 1 | —O— | 5 | —O— | phenyl | —O— | $-\overset{O}{\underset{}{C}}-$ | 3 | H | H | —COOCH$_3$ |
| 13 | pyridyl | 0 | —O— | 5 | —O— | phenyl | —O— | — | 4 | —CH$_3$ | —CH$_3$ | —COOC$_2$H$_5$ |
| 14 | pyridyl | 0 | — | 5 | —O— | phenyl | —O— | — | 4 | —CH$_3$ | —CH$_3$ | —COOC$_2$H$_5$ |

-continued $$A-(CH_2)_l-X^1-(CH_2)_m-X^2-B-X^3-Y-(CH_2)_n-\underset{R_2}{\overset{R_1}{\underset{|}{C}}}-R_3$$

| Example | A | l | X¹ | m | X² | B | X³ | Y | n | R₁ | R₂ | R₃ |
|---|---|---|---|---|---|---|---|---|---|---|---|---|
| 15 | pyrrolyl (N) | 0 | — | 5 | —O— | phenyl | —O— | — | 4 | —CH₃ | —CH₃ | —COOC₂H₅ |
| 16 | pyrazolyl | 0 | — | 5 | —O— | phenyl | —O— | — | 4 | —CH₃ | —CH₃ | —COOC₂H₅ |
| 17 | 2-pyridyl | 1 | —O— | 5 | —O— | phenyl | —O— | — | 4 | —CH₃ | —CH₃ | —COOC₂H₅ |
| 18 | 2-pyridyl | 2 | —O— | 5 | —O— | phenyl | —O— | — | 4 | —CH₃ | —CH₃ | —COOC₂H₅ |
| 19 | 4-pyridyl | 0 | —S— | 5 | —O— | phenyl | —O— | — | 4 | —CH₃ | —CH₃ | —COOC₂H₅ |
| 20 | N-methylimidazolyl | 0 | —S— | 5 | —O— | phenyl | —O— | — | 4 | —CH₃ | —CH₃ | —COOC₂H₅ |
| 21 | thiadiazolyl-S-CH₂COOC₂H₅ | 0 | —S— | 5 | —O— | phenyl | —O— | — | 4 | —CH₃ | —CH₃ | —COOC₂H₅ |

-continued $$A-(CH_2)_l-X^1-(CH_2)_m-X^2-B-X^3-Y-(CH_2)_n-\underset{R_2}{\overset{R_1}{\underset{|}{C}}}-R_3$$

| Example | A | l | $X^1$ | m | $X^2$ | B | $X^3$ | Y | n | $R_1$ | $R_2$ | $R_3$ |
|---------|---|---|-------|---|-------|---|-------|---|---|-------|-------|-------|
| 22 | N-N triazole with CH3 | 0 | —S— | 5 | —O— | phenyl | —O— | — | 4 | —CH₃ | —CH₃ | —COOC₂H₅ |
| 23 | 2-methylpyridine N-oxide | 0 | —S— | 5 | —O— | phenyl | —O— | — | 4 | —CH₃ | —CH₃ | —COOC₂H₅ |
| 24 | 2-methylpyrimidine | 0 | —S— | 5 | —O— | phenyl | —O— | — | 4 | —CH₃ | —CH₃ | —COOC₂H₅ |
| 25 | 2-methylthiazoline | 0 | —S— | 5 | —O— | phenyl | —O— | — | 4 | —CH₃ | —CH₃ | —COOC₂H₅ |
| 26 | 2-methylbenzothiazole | 0 | —S— | 5 | —O— | phenyl | —O— | — | 4 | —CH₃ | —CH₃ | —COOC₂H₅ |
| 27 | 2-methylbenzimidazole | 0 | —S— | 5 | —O— | phenyl | —O— | — | 4 | —CH₃ | —CH₃ | —COOC₂H₅ |

-continued
$$A-(CH_2)_l-X^1-(CH_2)_m-X^2-B-X^3-Y-(CH_2)_n-\underset{\underset{R_2}{|}}{\overset{\overset{R_1}{|}}{C}}-R_3$$
| Example | A | l | $X^1$ | m | $X^2$ | B | $X^3$ | Y | n | $R_1$ | $R_2$ | $R_3$ |
|---------|---|---|-------|---|-------|---|-------|---|---|-------|-------|-------|
| 28 | 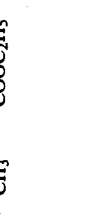 | 0 | —S— | 5 | —O— | 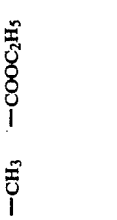 | —O— | — | 4 | —CH₃ | —CH₃ | —COOC₂H₅ |
| 29 |  | 0 | —S— | 5 | —O— |  | —O— | — | 4 | —CH₃ | —CH₃ | —COOC₂H₅ |
| 30 |  | 0 | —S— | 5 | —O— |  | —O— | — | 4 | —CH₃ | —CH₃ | —CONH₂ |
| 31 | 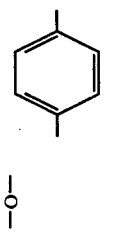 | 0 | —S— | 5 | —O— | 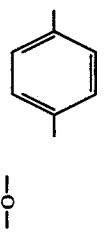 | —O— | — | 4 | —CH₃ | —CH₃ | —CONH₂ |
| 32 | 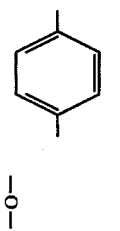 | 0 | —S— | 5 | —O— | 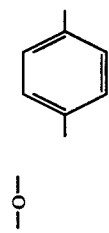 | —O— | — | 4 | —CH₃ | —CH₃ | —COOC₂H₅ |
| 33 | 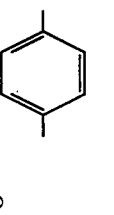 | 0 | —S— | 5 | —O— | 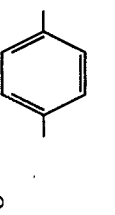 | —O— | — | 4 | —CH₃ | —CH₃ | —COOC₂H₅ |

-continued $$A-(CH_2)_l-X^1-(CH_2)_m-X^2-B-X^3-Y-(CH_2)_n-\underset{\underset{R_2}{|}}{\overset{\overset{R_1}{|}}{C}}-R_3$$

| Example | A | l | $X^1$ | m | $X^2$ | B | $X^3$ | Y | n | $R_1$ | $R_2$ | $R_3$ |
|---|---|---|---|---|---|---|---|---|---|---|---|---|
| 34 | 1,5-dimethyltetrazol-2-yl | 0 | —S— | 5 | —O— | 1,4-phenylene | —O— | — | 4 | —CH$_3$ | —CH$_3$ | —CONH$_2$ |
| 35 | 2-methylpyridin-6-yl | 0 | —O— | 5 | —O— | 1,4-phenylene | —O— | — | 4 | —CH$_3$ | —CH$_3$ | —COOC$_2$H$_5$ |
| 36 | benzimidazol-1-yl | 0 | — | 5 | —O— | 1,4-phenylene | —O— | — | 4 | —CH$_3$ | —CH$_3$ | —COOC$_2$H$_5$ |
| 37 | imidazol-1-yl | 0 | — | 5 | —O— | 1,3-phenylene | —O— | — | 4 | —CH$_3$ | —CH$_3$ | —COOC$_2$H$_5$ |
| 38 | 4-nitroimidazol-1-yl | 0 | — | 5 | —O— | 1,4-phenylene | —O— | — | 4 | —CH$_3$ | —CH$_3$ | —COOC$_2$H$_5$ |
| 39 | purin-9-yl | 0 | — | 5 | —O— | 1,4-phenylene | —O— | — | 4 | —CH$_3$ | —CH$_3$ | —COOC$_2$H$_5$ |

-continued
$$A-(CH_2)_l-X^1-(CH_2)_m-X^2-B-X^3-Y-(CH_2)_n-\underset{\underset{R_2}{|}}{\overset{\overset{R_1}{|}}{C}}-R_3$$
| Example | A | l | X¹ | m | X² | B | X³ | Y | n | R₁ | R₂ | R₃ |
|---|---|---|---|---|---|---|---|---|---|---|---|---|
| 40 | 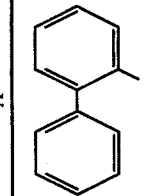 | 0 | — | 5 | —O— | 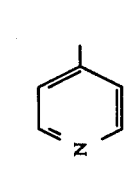 | —O— | — | 4 | —CH₃ | —CH₃ | —COOC₂H₅ |
| 41 | 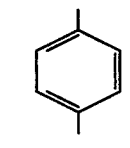 | 0 | — | 5 | —O— | 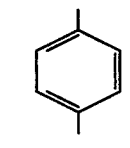 | —O— | — | 4 | —CH₃ | —CH₃ | —COOC₂H₅ |
| 42 | 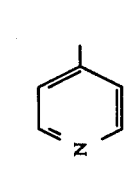 | 0 | — | 5 | —S— | 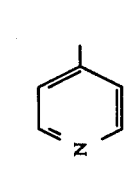 | —S— | — | 4 | —CH₃ | —CH₃ | —COOC₂H₅ |
| 43 | 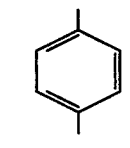 | 0 | —S— | 5 | —O— | 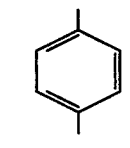 | —O— | — | 4 | —CH₃ | —CH₃ | —COOC₂H₅ |
| 44 | 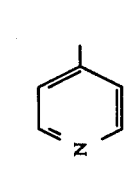 | 0 | —S— | 5 | —O— | 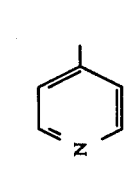 | —O— | — | 4 | —CH₃ | —CH₃ | —CONH₂ |
| 45 | 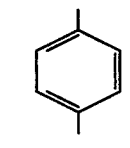 | 0 | — | 5 | —O— | 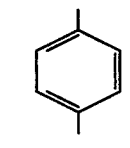 | —O— | — | 4 | —CH₃ | —CH₃ | —COOH |
| 46 | 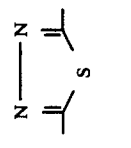 | 0 | — | 5 | —O— | 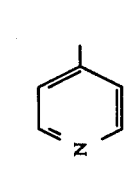 | —O— | — | 4 | —CH₃ | —CH₃ | —COOH |

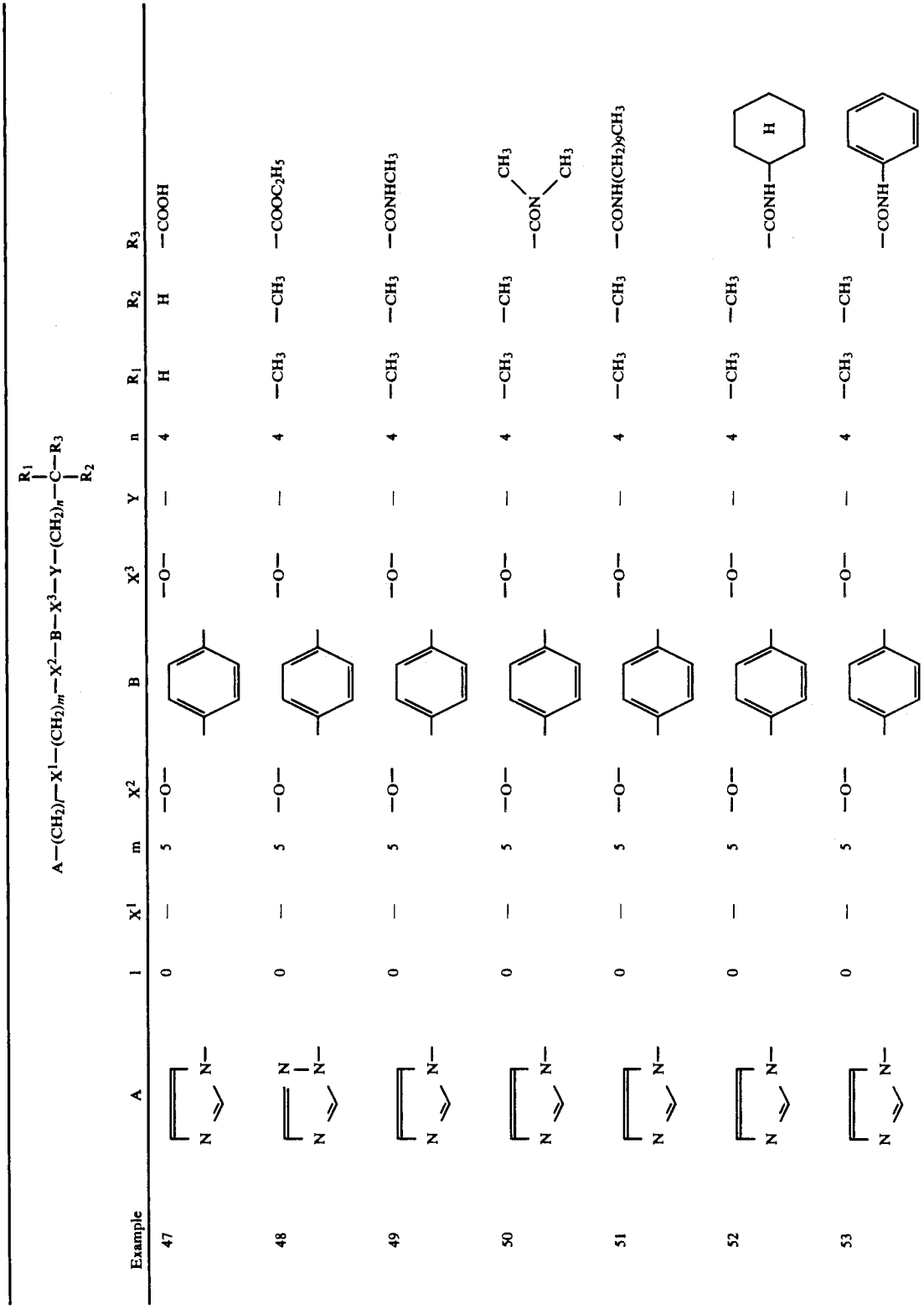

-continued
$$A-(CH_2)_l-X^1-(CH_2)_m-X^2-B-X^3-Y-(CH_2)_n-\underset{\underset{R_2}{|}}{\overset{\overset{R_1}{|}}{C}}-R_3$$
| Example | A | l | $X^1$ | m | $X^2$ | B | $X^3$ | Y | n | $R_1$ | $R_2$ | $R_3$ |
|---|---|---|---|---|---|---|---|---|---|---|---|---|
| 54 | 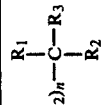 | 0 | — | 5 | —O— | 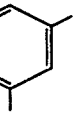 | —O— | — | 4 | —CH$_3$ | —CH$_3$ | —CONH$_2$ |
| 55 | 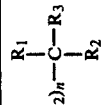 | 0 | — | 5 | —O— | 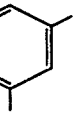 | —O— | — | 4 | —CH$_3$ | —CH$_3$ | —CN |
| 56 | 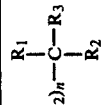 | 0 | — | 5 | —O— | 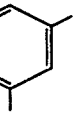 | —O— | — | 4 | H | H | —CONH$_2$ |
| 57 | 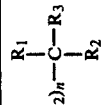 | 0 | — | 5 | —O— | 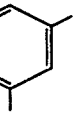 | —O— | — | 4 | —CH$_3$ | —CH$_3$ | —COOC$_2$H$_5$ |
| 57 | 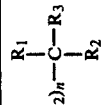 | 0 | — | 5 | —O— | 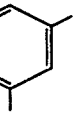 | —O— | — | 4 | —CH$_3$ | —CH$_3$ | —COOH |
| 58 | 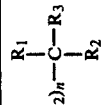 | 0 | — | 5 | —O— | 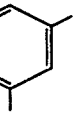 | —S— | — | 4 | —CH$_3$ | —CH$_3$ | —COOC$_2$H$_5$ |
| 58 | 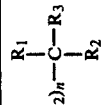 | 0 | — | 5 | —O— | 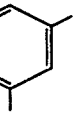 | $-\overset{O}{\underset{}{\overset{\|}{S}}}-$ | — | 4 | —CH$_3$ | —CH$_3$ | —COOC$_2$H$_5$ |

-continued
$$A-(CH_2)_l-X^1-(CH_2)_m-X^2-B-X^3-Y-(CH_2)_n-\overset{\overset{R_1}{|}}{\underset{\underset{R_2}{|}}{C}}-R_3$$
| Example | A | l | $X^1$ | m | $X^2$ | B | $X^3$ | Y | n | $R_1$ | $R_2$ | $R_3$ |
|---------|---|---|-------|---|-------|---|-------|---|---|-------|-------|-------|
| 59 | 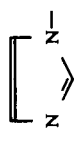 | 0 | — | 5 | —O— | 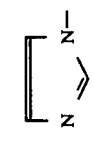 | —S— | — | 4 | —CH$_3$ | —CH$_3$ | —COOC$_2$H$_5$ |
| 59 | 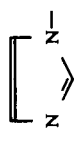 | 0 | — | 5 | —O— | 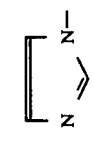 | $\overset{O}{\underset{\underset{}{\|}}{-S-}}$ | — | 4 | —CH$_3$ | —CH$_3$ | —COOC$_2$H$_5$ |
| 60 | 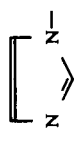 | 0 | — | 5 | —O— | 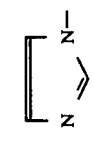 | —O— | — | 4 | —CH$_3$ | —CH$_3$ | —COOC$_2$H$_5$ |
| 61 | 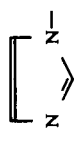 | 0 | — | 5 | —O— | 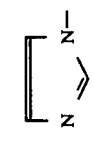 | —O— | — | 4 | —CH$_3$ | —CH$_3$ | —CONH(CH$_2$)$_6$CH$_3$ |

We claim:
1. A method of treating tumors in a patient which comprises administering to said patient an anti-tumor effective amount of a pharmaceutical composition comprised of from about 500 to about 2,000 mg of 6-[p-[5-(1-imidazolyl)pentyloxy]phenoxy]-2,2-dimethylhexanoic acid and a pharmaceutically acceptable excipient.

* * * * *